US012544249B2

(12) United States Patent
Deren et al.

(10) Patent No.: US 12,544,249 B2

(45) Date of Patent: Feb. 10, 2026

(54) INFLATABLE STENT FOR MEDICAL TREATMENT

(71) Applicant: SafeSplints, LLC, Winter Park, FL (US)

(72) Inventors: Jeffrey Deren, Winter Park, FL (US); Evan Gomez, Orlando, FL (US); Anthony Mango, Orlando, FL (US); Paul Reiss, Orlando, FL (US); Miguel Leon, Orlando, FL (US); Meng Tia, Orlando, FL (US)

(73) Assignee: SafeSplints, LLC, Winter Park, FL (US)

( * ) Notice: Subject to any disclaimer, the term of this patent is extended or adjusted under 35 U.S.C. 154(b) by 515 days.

(21) Appl. No.: 18/076,844

(22) Filed: Dec. 7, 2022

(65) Prior Publication Data

US 2023/0099955 A1 Mar. 30, 2023

Related U.S. Application Data

(63) Continuation-in-part of application No. 16/883,687, filed on May 26, 2020, now abandoned, which is a
(Continued)

(51) Int. Cl.
*A61F 5/058* (2006.01)

(52) U.S. Cl.
CPC ...... *A61F 5/05816* (2013.01); *A61F 5/05858* (2013.01); *A61F 5/05866* (2013.01)

(58) Field of Classification Search
CPC .... A61F 5/0118; A61F 5/013; A61F 5/05866; A61F 5/05875; A61F 2007/0035; A61F 2007/0036; A61F 5/0111; A61F 5/05858; A61F 13/104; A61F 2007/0037; A61F 2007/0045; A61F 2007/023; A61F 2/586;
(Continued)

(56) References Cited

U.S. PATENT DOCUMENTS

| | | | |
|---|---|---|---|
| 4,281,647 | A | 8/1981 | Antypas |
| 5,152,740 | A | 10/1992 | Harkensee et al. |

(Continued)

OTHER PUBLICATIONS

International Searching Authority, International Search Report, PCT/US2017/040022, Dated Sep. 14, 2017.

(Continued)

*Primary Examiner* — Ophelia A Hawthorne

(74) *Attorney, Agent, or Firm* — Reichel Stohry Dean LLP; Mark C. Reichel; Natalie J. Dean

(57) ABSTRACT

An inflatable splint can include a sleeve shaped to conform to a specific human body part and a plurality of inflatable chambers disposed on the sleeve. The sleeve, in cooperation with the plurality of chambers in an inflated condition, can be contoured to maintain the specific human body part in a desired position. A method of using an inflatable splint includes admitting a body part into a sleeve of the inflatable splint and positioning the sleeve around the body part. One or more of the plurality of air chambers are selectively inflated such that the flexible sleeve in cooperation with the plurality of chambers in inflated condition is contoured and positioned to maintain the specific human body part in a desired position.

20 Claims, 29 Drawing Sheets

Related U.S. Application Data continuation of application No. 15/637,794, filed on Jun. 29, 2017, now Pat. No. 10,660,782.

(60) Provisional application No. 62/356,664, filed on Jun. 30, 2016.

(58) Field of Classification Search

CPC .. A61F 5/0106; A61F 5/0123; A61F 5/05816; A61F 5/012; A61F 5/0102; A61F 5/0127; A61F 2007/0032; A61F 5/05841; A61F 5/32; A61F 2007/0091; A61F 13/064; A61F 2007/003; A61F 2007/0039; A61F 5/3723; A61F 5/3761; A61F 5/10; A61F 5/30; A61F 5/058; A61H 2201/1697; A61H 2205/12; A61H 2201/1635; A61H 2201/164; A61H 1/024; A61H 1/0266; A61H 1/0274; A61H 1/0277; A61H 1/0285; A61H 1/0288; A61H 2201/0103; A41D 13/088; A61B 17/135

See application file for complete search history.

(56) References Cited

U.S. PATENT DOCUMENTS

| | | | |
|---|---|---|---|
| 5,427,577 | A | 6/1995 | Picchietti et al. |
| 6,000,059 | A | 12/1999 | Abts |
| 6,146,347 | A | 11/2000 | Porrata |
| 6,719,711 | B1 | 4/2004 | Islava |
| 10,660,782 | B2 | 5/2020 | Deren |
| 2002/0116743 | A1 | 8/2002 | Tourbier et al. |
| 2008/0058911 | A1 | 3/2008 | Parish et al. |
| 2011/0201981 | A1 | 8/2011 | Deshpande et al. |
| 2013/0053739 | A1 | 2/2013 | Mustafa |
| 2016/0081843 | A1 | 3/2016 | Eriksson |
| 2024/0016648 | A1* | 1/2024 | Arsiwala ............. A61F 5/05816 |

OTHER PUBLICATIONS

International Searching Authority, Written Opinion of the International Searching Authority, PCT/US2017/040022, Dated Sep. 14, 2017.

* cited by examiner

*FIG.* 30

INFLATABLE STENT FOR MEDICAL TREATMENT

PRIORITY AND CROSS-REFERENCE TO RELATED APPLICATIONS

The present application is related to, claims the priority benefit of, and is a U.S. continuation-in-part patent application of, U.S. patent application Ser. No. 16/883,687, filed May 26, 2020, which is related to, claims the priority benefit of, and is a U.S. continuation patent application of, U.S. patent application Ser. No. 15/637,794, filed Jun. 29, 2017 and issued as U.S. Pat. No. 10,660,782 on May 26, 2020, which is related to, and claims the priority benefit of, U.S. Provisional Patent Application Ser. No. 62/356,664, filed on Jun. 30, 2016. The contents of each of these patent applications are incorporated herein directly and by reference in their entirety.

FIELD OF THE INVENTION

The present invention relates to inflatable splints, and more particularly, to an inflatable splint for medical treatment.

BACKGROUND OF THE INVENTION

Paramedics and other emergency response personnel often utilize emergency immobilization splints for arms and legs for patient transport. Such devices cannot, however, maintain an extremity in a particular position, especially a hand. Splints made of plaster and fiberglass can be used for this purpose, but they must be applied by trained medical personnel. In practice, however, such splints are often applied inappropriately, the limb is not positioned well or the splint is too tight, etc.—potentially worsening a patient's condition before the patient can be seen a specialist. Other disadvantages of current splints include overall bulkiness and cumbersomeness when applying the splint to a limb. After the splint has been applied, a patient is usually unable adjust the splint appropriately. The cost of manufacture for current splints is comparatively high. Further advances in medical splint technology are possible.

BRIEF SUMMARY OF THE INVENTION

In view of the foregoing, it is an object of the present invention to provide an inflatable splint for medical treatment. According to one embodiment of the present invention, the inflatable splint can include a sleeve shaped to conform to a specific human body part and a plurality of Inflatable chambers disposed on the sleeve. The sleeve, in cooperation with the plurality of chambers in an inflated condition, can be contoured to maintain the specific human body part in a desired position.

According to another embodiment of the present invention, a method of using an inflatable splint includes admitting a body part into a sleeve of the inflatable splint and positioning the sleeve around the body part. One or more of the plurality of air chambers are selectively inflated such that the flexible sleeve in cooperation with the plurality of chambers in inflated condition is contoured and positioned to maintain the specific human body part in a desired position.

According to another embodiment of the present invention, a method of making an inflatable splint includes determining locations of a plurality of air chambers on a sheet and positioning respective molds of predetermined dimension on the determined locations of the plurality of air chambers. The plurality of air chambers are formed on the sheet based on the respective molds at the determined locations. One or more loops and fasteners are attached on at least one longitude edge of the sheet.

The present disclosure also includes disclosure of an inflatable splint comprising a volar portion comprising a first volar arm chamber, a second volar arm chamber, and a third volar arm chamber, each parallel to one another, a dorsal portion comprising a first dorsal arm chamber, a second dorsal arm chamber, and a third dorsal chamber, each parallel to one arm another, a plurality of hand chambers adjacent the first dorsal arm chamber, the second dorsal arm chamber, and the third dorsal arm chamber, and a first forearm stabilization strap extending from the dorsal portion and configured to wrap around the splint when the splint is worn by a user.

The present disclosure includes disclosure of an inflatable splint, wherein when the splint is worn by a user and when each of the first volar arm chamber, the second volar arm chamber, and the third volar arm chamber are inflated, a lengthwise volar portion of a forearm is stabilized by the splint.

The present disclosure includes disclosure of an inflatable splint, wherein a first volar valve is configured to inflate each of the first volar arm chamber, the second volar arm chamber, and the third volar arm chamber.

The present disclosure includes disclosure of an inflatable splint, wherein when the splint is worn by a user and when wherein each of the first dorsal arm chamber, the second dorsal arm chamber, and the third dorsal arm chamber are inflated, a lengthwise dorsal portion of a forearm is stabilized by the splint.

The present disclosure includes disclosure of an inflatable splint, wherein a first dorsal valve is configured to inflate each of the first dorsal arm chamber, the second dorsal arm chamber, and the third dorsal arm chamber.

The present disclosure includes disclosure of an inflatable splint, wherein when the splint is worn by a user and when each of the plurality of hand chambers are inflated, a back of a hand of the user is stabilized by the splint.

The present disclosure includes disclosure of an inflatable splint, wherein the first volar valve is further configured to inflate the plurality of hand chambers.

The present disclosure includes disclosure of an inflatable splint, further comprising a palm portion comprising a plurality of palm chambers.

The present disclosure includes disclosure of an inflatable splint, wherein when the splint is worn by a user and when each of the plurality of palm chambers are inflated, a palm of a hand of the user is stabilized by the splint.

The present disclosure includes disclosure of an inflatable splint, further comprising a plurality of hook and loop fastener portions positioned upon the splint.

The present disclosure includes disclosure of an inflatable splint, wherein the first forearm stabilization strap is configured to wrap around the splint when the splint is worn by a user and to be secured to the splint using at least one hook and loop fastener portion of the hook and loop fastener portions.

The present disclosure includes disclosure of an inflatable splint, further comprising a second forearm stabilization strap extending from the dorsal portion and configured to wrap around the splint when the splint is worn by a user.

The present disclosure includes disclosure of an inflatable splint, wherein the second forearm stabilization strap is configured to wrap around the splint when the splint is worn by a user and to be secured to the splint using at least one hook and loop fastener portion of the hook and loop fastener portions.

The present disclosure includes disclosure of an inflatable splint, wherein the volar portion and the dorsal portion are coupled to one another via a connection portion located therebetween.

The present disclosure includes disclosure of an inflatable splint, comprising a volar portion comprising a first volar arm chamber, a second volar arm chamber, a third volar arm chamber, a fourth volar arm chamber, and a fifth volar arm chamber, each parallel to one another, a dorsal portion comprising a first dorsal arm chamber, a second dorsal arm chamber, and a third dorsal chamber, each parallel to one arm another, a plurality of hand chambers adjacent the first dorsal arm chamber, the second dorsal arm chamber, and the third dorsal arm chamber, and a first forearm stabilization strap and a second forearm stabilization strap, each extending from the dorsal portion and configured to wrap around the splint when the splint is worn by a user, wherein when the splint is worn by a user and when each of the first volar arm chamber, the second volar arm chamber, and the third volar arm chamber are inflated, a lengthwise volar portion of a forearm is stabilized by the splint, wherein a first volar valve is configured to inflate each of the first volar arm chamber, the second volar arm chamber, and the third volar arm chamber, wherein when the splint is worn by a user and when wherein each of the first dorsal arm chamber, the second dorsal arm chamber, and the third dorsal arm chamber are inflated, a lengthwise dorsal portion of a forearm is stabilized by the splint, and wherein a first dorsal valve is configured to inflate each of the first dorsal arm chamber, the second dorsal arm chamber, and the third dorsal arm chamber.

The present disclosure includes disclosure of an inflatable splint, wherein when the splint is worn by a user and when each of the plurality of hand chambers are inflated, a back of a hand of the user is stabilized by the splint, and wherein the first dorsal valve is further configured to inflate the plurality of hand chambers.

The present disclosure includes disclosure of an inflatable splint, further comprising a palm portion comprising a plurality of palm chambers, and wherein when the splint is worn by a user and when each of the plurality of palm chambers are inflated, a palm of a hand of the user is stabilized by the splint.

The present disclosure includes disclosure of an inflatable splint, further comprising a plurality of hook and loop fastener portions positioned upon the splint, and wherein the first forearm stabilization strap and the second forearm stabilization strap are configured to wrap around the splint when the splint is worn by a user and to be secured to the splint using at least one hook and loop fastener portion of the hook and loop fastener portions.

The present disclosure includes disclosure of an inflatable splint, wherein the volar portion and the dorsal portion are coupled to one another via a connection portion located therebetween.

The present disclosure includes disclosure of a method of stabilizing a forearm, comprising the steps of positioning the inflatable splint of claim 1 around a forearm of a user, securing the splint about the forearm using the first forearm stabilization strap, and inflating each of the first dorsal arm chamber, the second dorsal arm chamber, the third dorsal arm chamber, the first volar arm chamber, the second volar arm chamber, and the third volar arm chamber to stabilize the forearm using the splint.

The present disclosure includes disclosure of an inflatable splint, comprising a volar portion comprising a plurality of volar arm chambers, each parallel to one another, a dorsal portion comprising a plurality of dorsal arm chambers, each parallel to one arm another, a plurality of hand chambers adjacent the plurality of dorsal arm chambers, and a first forearm stabilization strap extending from the dorsal portion and configured to wrap around the splint when the splint is worn by a user.

The present disclosure includes disclosure of an inflatable splint, wherein when the splint is worn by a user and when each volar arm chamber of the plurality of volar arm chambers are inflated, a lengthwise volar portion of a forearm is stabilized by the splint.

The present disclosure includes disclosure of an inflatable splint, wherein a first volar valve is configured to inflate each of the volar arm chambers of the plurality of volar arm chambers.

The present disclosure includes disclosure of an inflatable splint, wherein when the splint is worn by a user and when wherein each dorsal arm chamber of the plurality of dorsal arm chambers are inflated, a lengthwise dorsal portion of a forearm is stabilized by the splint.

The present disclosure includes disclosure of an inflatable splint, wherein a first dorsal valve is configured to inflate each of the dorsal arm chambers of the plurality of dorsal arm chambers.

The present disclosure includes disclosure of an inflatable splint, wherein when the splint is worn by a user and when each of the plurality of hand chambers are inflated, a back of a hand of the user is stabilized by the splint.

The present disclosure includes disclosure of an inflatable splint, wherein the first dorsal valve is further configured to inflate the plurality of hand chambers.

The present disclosure includes disclosure of an inflatable splint, further comprising a palm portion comprising a plurality of palm chambers, the palm portion adjacent the plurality of volar arm chambers, and wherein when the splint is worn by a user and when each of the plurality of palm chambers are inflated, a palm of a hand of the user is stabilized by the splint.

The present disclosure includes disclosure of an inflatable splint, further comprising a forearm bladder having an inflation tube coupled thereto, the forearm bladder coupled to an inner portion of the splint and configured for inflation while the splint is worn by the user so to further stabilize the arm at or near a wrist.

The present disclosure includes disclosure of an inflatable splint, further comprising a plurality of hook and loop fastener portions positioned upon the splint.

The present disclosure includes disclosure of an inflatable splint, wherein the first forearm stabilization strap is configured to wrap around the splint when the splint is worn by a user and to be secured to the splint using at least one hook and loop fastener portion of the hook and loop fastener portions.

The present disclosure includes disclosure of an inflatable splint, further comprising a second forearm stabilization strap extending from the dorsal portion and configured to wrap around the splint when the splint is worn by a user.

The present disclosure includes disclosure of an inflatable splint, wherein the second forearm stabilization strap is configured to wrap around the splint when the splint is worn by a user and to be secured to the splint using at least one hook and loop fastener portion of the hook and loop fastener portions.

The present disclosure includes disclosure of an inflatable splint, wherein the volar portion and the dorsal portion are coupled to one another via a connection portion located therebetween.

The present disclosure includes disclosure of an inflatable splint, comprising a volar portion comprising a first volar arm chamber, a second volar arm chamber, a third volar arm chamber, a fourth volar arm chamber, and a fifth volar arm chamber, each parallel to one another, a dorsal portion comprising a first dorsal arm chamber, a second dorsal arm chamber, and a third dorsal chamber, each parallel to one arm another, a plurality of hand chambers adjacent the first dorsal arm chamber, the second dorsal arm chamber, and the third dorsal arm chamber, and a first forearm stabilization strap and a second forearm stabilization strap, each extending from the dorsal portion and configured to wrap around the splint when the splint is worn by a user; wherein when the splint is worn by a user and when each of the first volar arm chamber, the second volar arm chamber, the third volar arm chamber, the fourth volar arm chamber, and the fifth volar arm chamber are inflated, a lengthwise volar portion of a forearm is stabilized by the splint, wherein a first volar valve is configured to inflate each of the first volar arm chamber, the second volar arm chamber, and the third volar arm chamber, wherein when the splint is worn by a user and when wherein each of the first dorsal arm chamber, the second dorsal arm chamber, and the third dorsal arm chamber are inflated, a lengthwise dorsal portion of a forearm is stabilized by the splint, and wherein a first dorsal valve is configured to inflate each of the first dorsal arm chamber, the second dorsal arm chamber, and the third dorsal arm chamber.

The present disclosure includes disclosure of an inflatable splint, wherein when the splint is worn by a user and when each of the plurality of hand chambers are inflated, a back of a hand of the user is stabilized by the splint, and wherein the first dorsal valve is further configured to inflate the plurality of hand chambers.

The present disclosure includes disclosure of an inflatable splint, further comprising a palm portion comprising a plurality of palm chambers, and wherein when the splint is worn by a user and when each of the plurality of palm chambers are inflated, a palm of a hand of the user is stabilized by the splint.

The present disclosure includes disclosure of an inflatable splint, further comprising a plurality of hook and loop fastener portions positioned upon the splint, and wherein the first forearm stabilization strap and the second forearm stabilization strap are configured to wrap around the splint when the splint is worn by a user and to be secured to the splint using at least one hook and loop fastener portion of the hook and loop fastener portions.

The present disclosure includes disclosure of an inflatable splint, wherein the volar portion and the dorsal portion are coupled to one another via a connection portion located therebetween.

These and other objects, aspects and advantages of the present invention will be better appreciated in view of the drawings and following detailed description of preferred embodiments.

DETAILED DESCRIPTION

According to one embodiment of the present invention, an inflatable splint is used for limb immobilization or traction. The inflatable splint includes a sleeve portion shaped to conform to a specific human body part (e.g., a hand, a foot, a leg, an arm, a joint, etc.) and a plurality of tubular chambers contoured and positioned to provide optimum support for certain area of the specific body part. With reference to FIGS. 1-23, the assembly of the structural elements and further features thereof will be described here. These structural elements are selected for exemplary and illustrative purposes, and it will be appreciated the present invention is not necessarily limited thereto.

Figure 1:
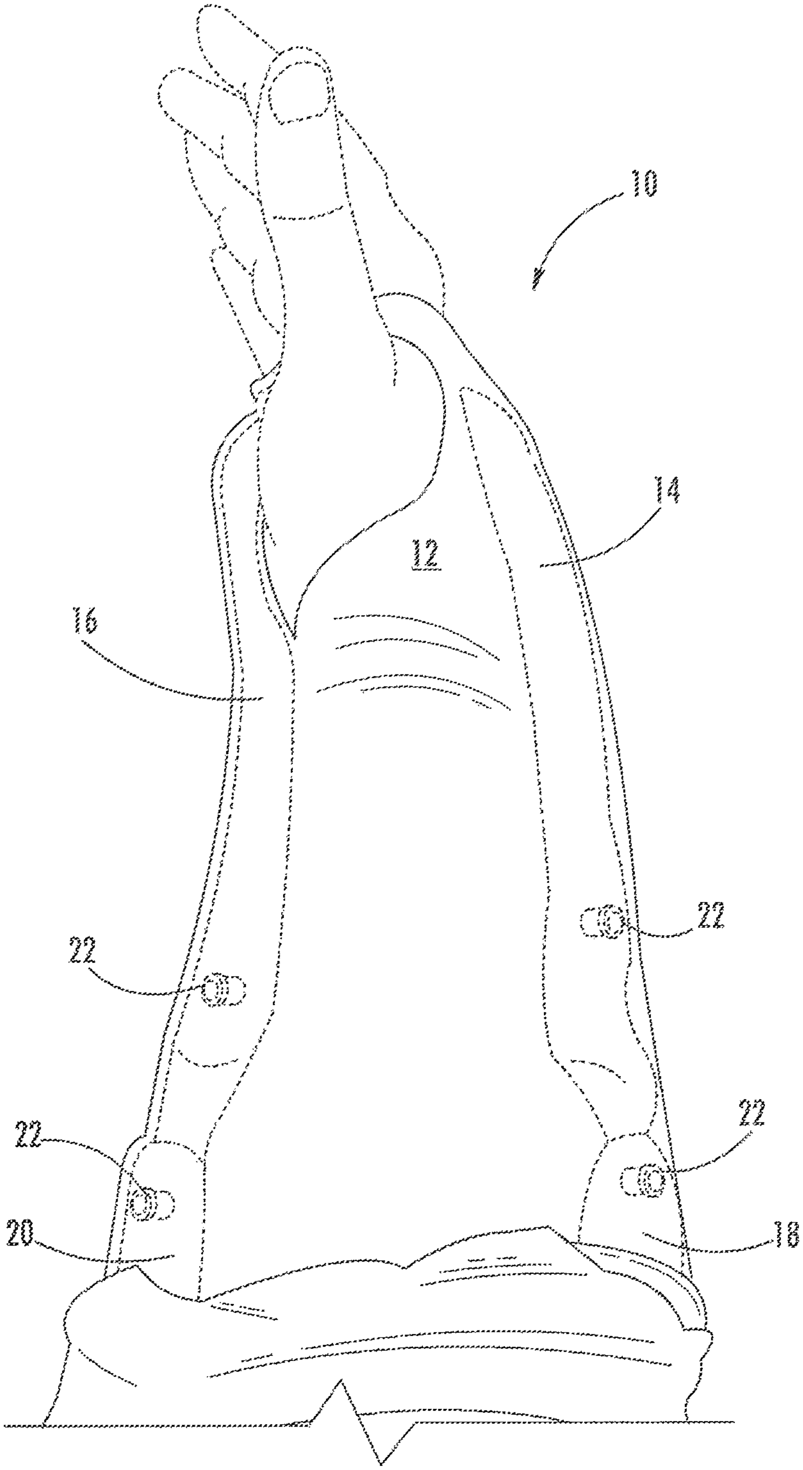
FIG. 1 is a perspective view of dorsal side and ventral side of a forearm and a hand applied with an inflatable splint, according to one embodiment of the present invention.
Figure 2:
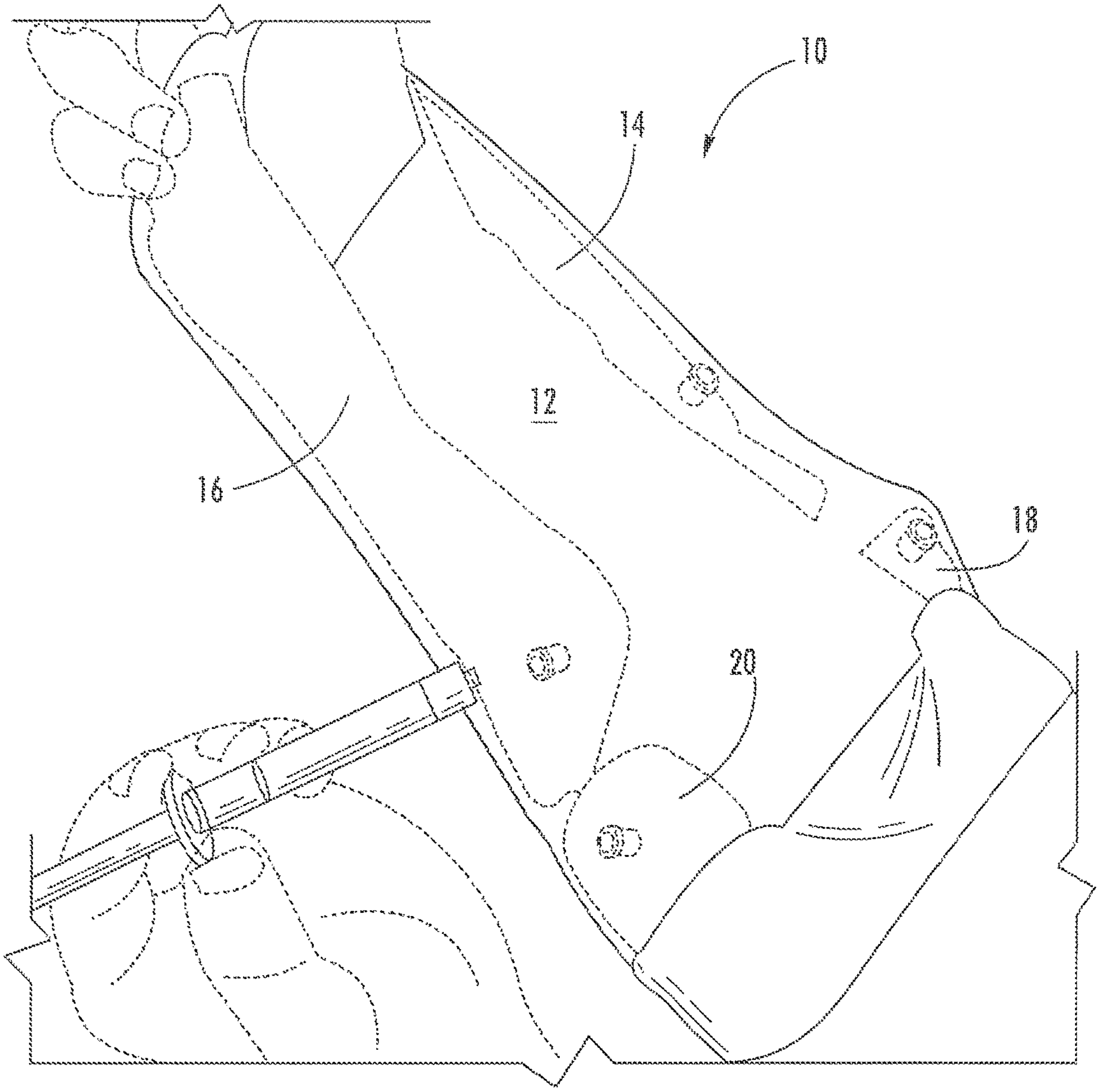
FIG. 2 is perspective view of the ventral side of a forearm and a hand applied with the inflatable splint of FIG. 1.

In one embodiment, referring to FIGS. 1-2, an exemplary inflatable splint 10 can be used for an arm and/or a hand of a patient. The inflatable splint 10 includes a sleeve 12 shaped to conform a forearm and four separately inflatable lengthwise tubular chambers 14, 16, 18 and 20. A patient's forearm is admitted into the sleeve 12, which is then secured to the palm between the thumb and the index finger. In the depicted embodiment, the first chamber 14 surrounds a portion of the dorsal side of the hand and the lower forearm, the second chamber 16 surrounds a portion of the palmar side of the hand and the lower forearm, the third chamber 18 surrounds the dorsal side of the upper forearm, and the fourth chamber 20 surrounds the palmar side of the upper forearm. The plurality of conjoined air chambers 14, 16, 18 and 20 can surround at least a portion of the radius and the ulna bones in the forearm and/or at least a portion of dorsal side or palmar side of the hand to provide a desired position and/or orientation for the forearm and/or hand.

Each of the plurality of chambers 14, 16, 18 and 20 can be inflated independently via a port with a suitable valve 22 for introducing air into the respective chambers. Adjacent chamber cells can also be connected for air flow communication at their ends by restricted passageways. An advantage of valve 22 is a stem to enable the air chambers to be inflated by mouth, a pump, a syringe, or other mechanical means. Any of various valve constructions known to the art can be used. The degree of compression can be controlled by the pressure to which the bandage splint is inflated.

The air chambers in any particular case can have different shapes and sizes, depending on the type of injury and the specific body part to be immobilized. In the depicted embodiments, the air chambers are generally rectangular in shape with rounded corners. The air chambers are shaped and arranged such that the body part is immobilized at its neutral position and/or held at the desired angle and/or orientation in relation to other body parts. Right limbs could require different splints from left limbs.

Figure 3:
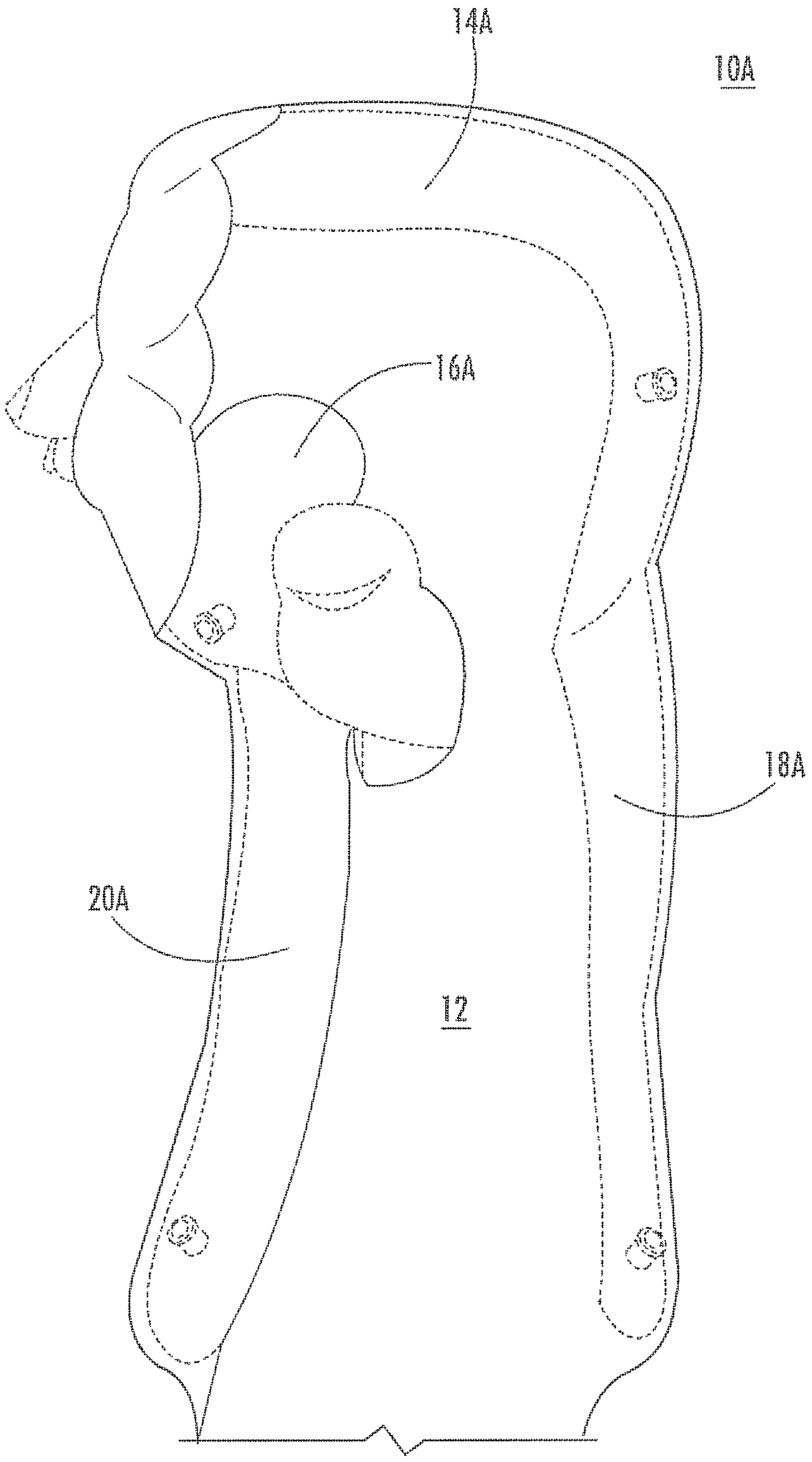
FIG. 3 is a perspective view of dorsal side and ventral side of a forearm and a hand applied with an inflatable splint, according to another embodiment of the present invention.
Figure 4:
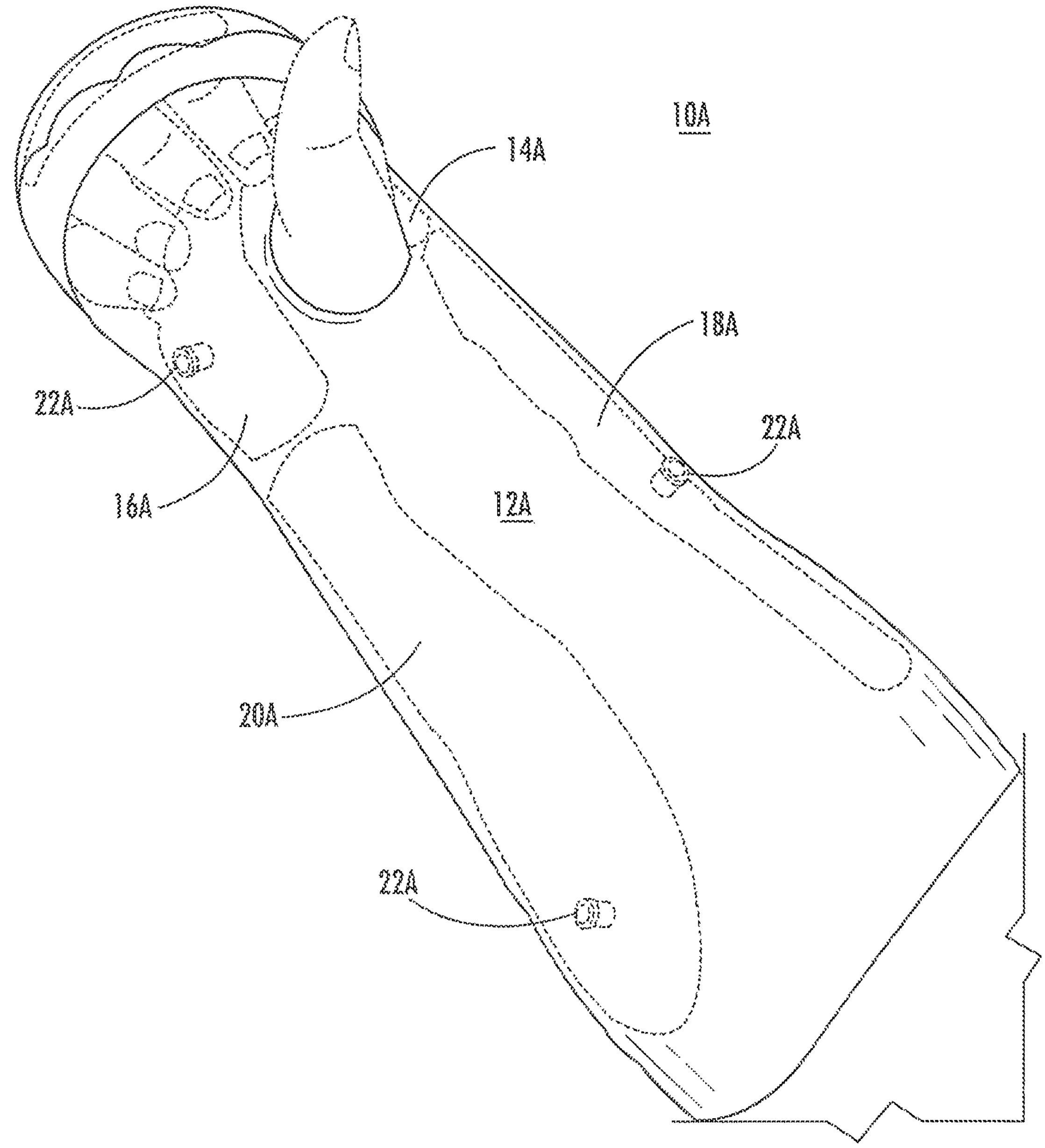
FIG. 4 is a perspective view of the ventral side of a forearm and a hand applied with the inflatable splint of FIG. 3.

In another embodiment, referring to FIGS. 3-4, an inflatable splint 10A adapted for immobilizing a patient's hand and forearm includes a sleeve 12A and four lengthwise-extending tubular chambers: a first chamber 14A surrounding a portion of the dorsal side of a hand, a second chamber 16A surrounding a portion of the palmar side of the hand, a third chamber 18A surrounding the dorsal side of a forearm, and a fourth chamber 20A surrounding the palmar side of the forearm. The chambers 14 and 16 are conjoined and adapted to fit to the upper arm and in the palm of a patient's hand between the thumb and fingers. Additional straps, such as Velcro straps or other connecting methods, can be used for further securing the splint 10A to its intended position and/or orientation. The additional straps can be further adjusted to fit the dimension of a limb and/or joint.

Figure 5:
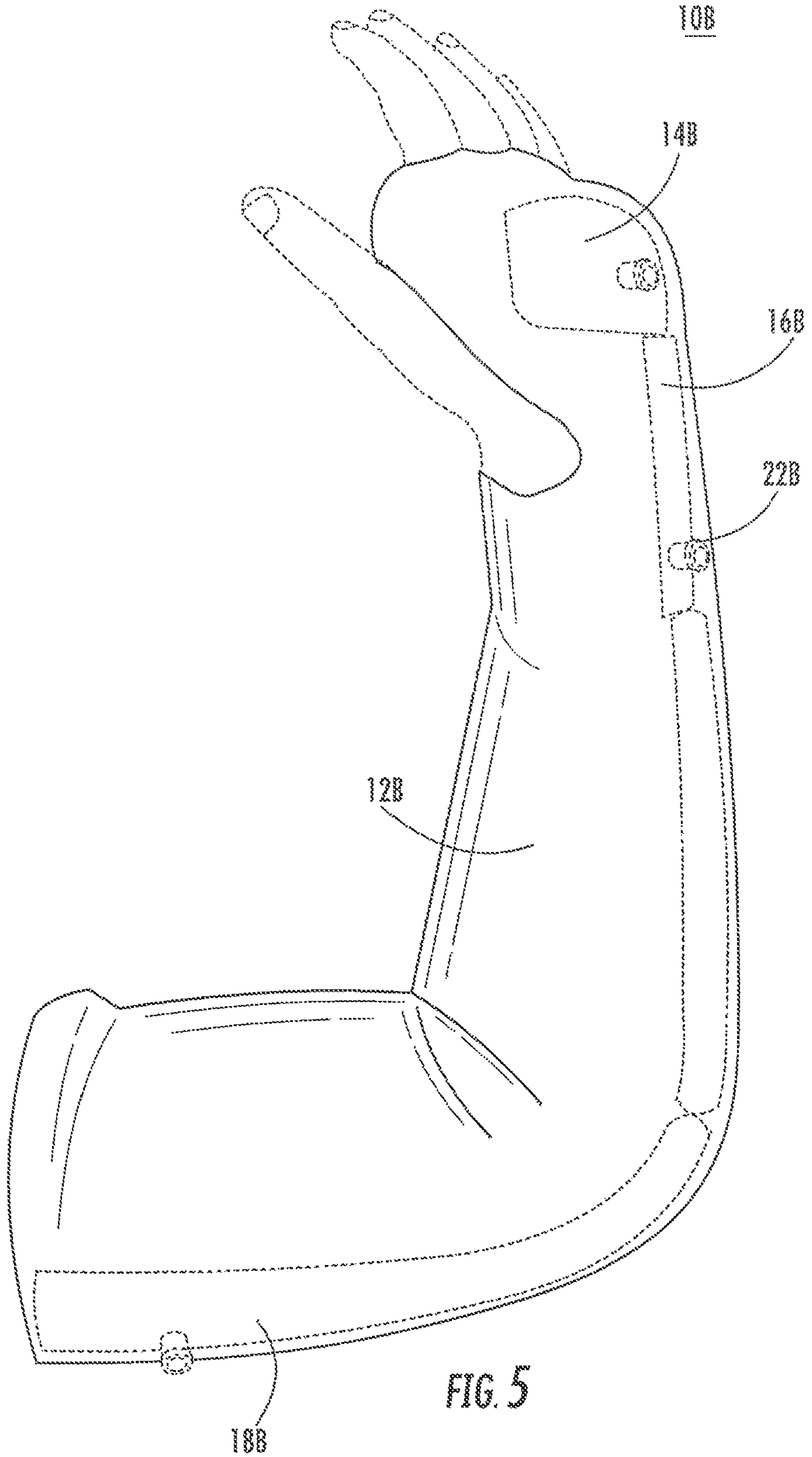
FIG. 5 is a perspective view of dorsal side of a forearm and a hand applied with an inflatable splint, according to yet another embodiment of the present invention.
Figure 6:
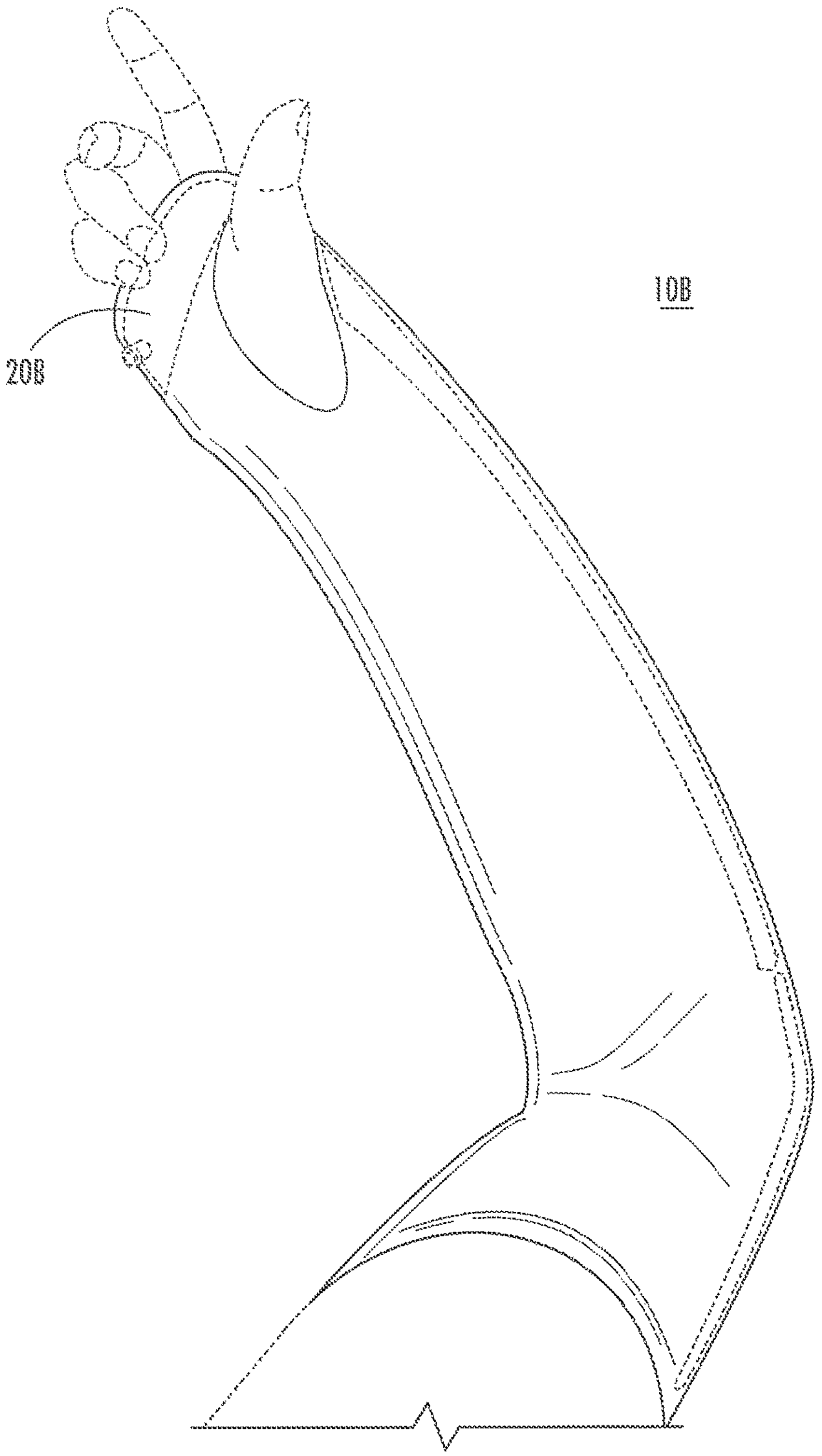
FIG. 6 is a perspective view of the ventral side of a forearm and a land applied with the inflatable splint of FIG. 5.

In yet another embodiment, referring to FIGS. 5-6, an inflatable splint 10B used for a patient's hand, wrist, forearm and/or elbow includes a sleeve 12B and four lengthwise-extending tubular chambers; a first chamber 14B surrounding a portion of the dorsal side of a hand, a second chamber 16B surrounding the dorsal side of a lower arm, a third chamber 18B surrounding the dorsal side of an upper arm, and a fourth chamber 20B surrounding the palmar side of the hand.

Figure 7:
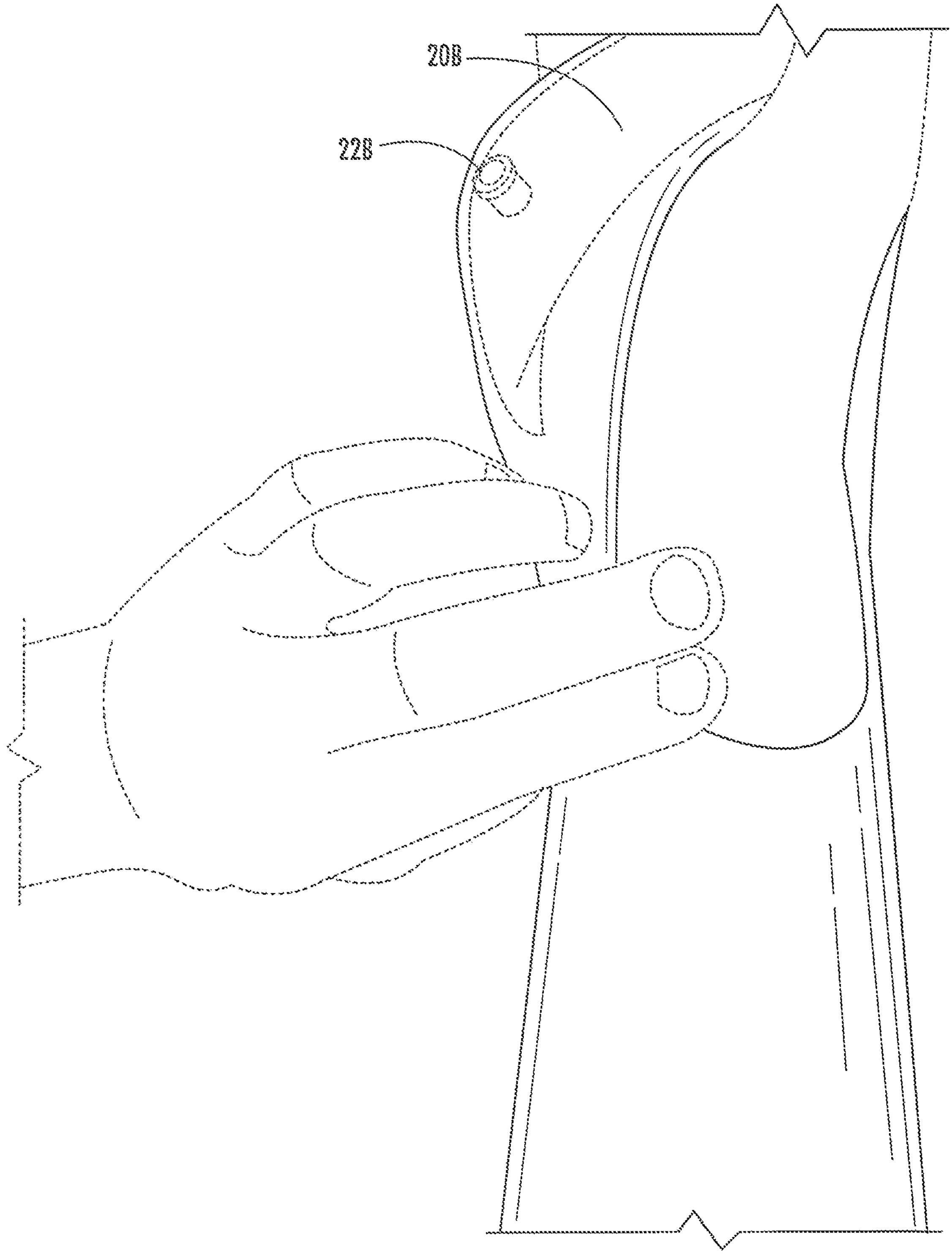
FIG. 7 is a perspective view of the ventral side of a forearm applied with an inflatable splint, leaving the pulse checking area accessible, according to another embodiment of the present invention.
Figure 8:
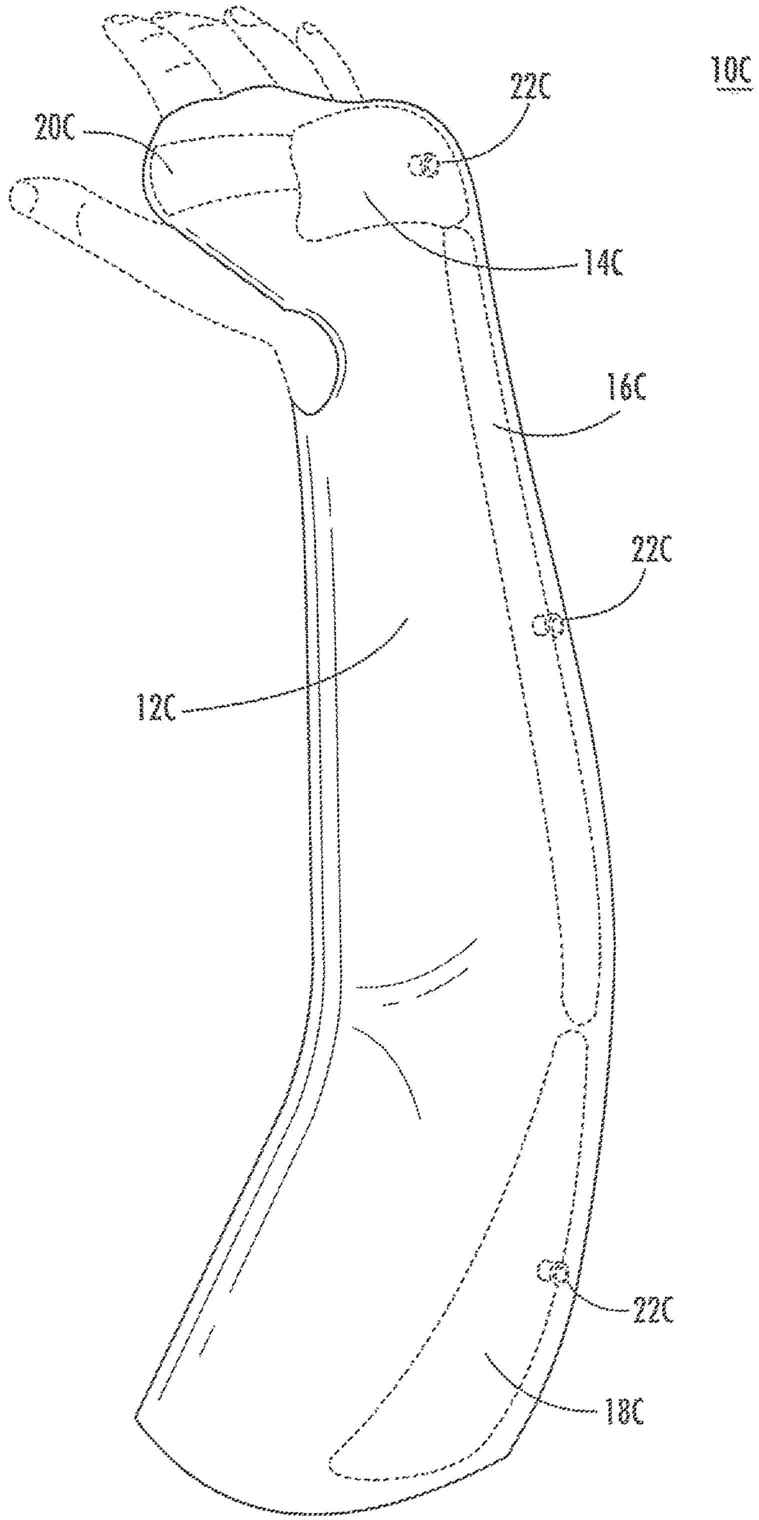
FIG. 8 is a perspective view of dorsal side of a forearm and a hand applied with an inflatable splint, according to yet another embodiment of the present invention.
Figure 9:
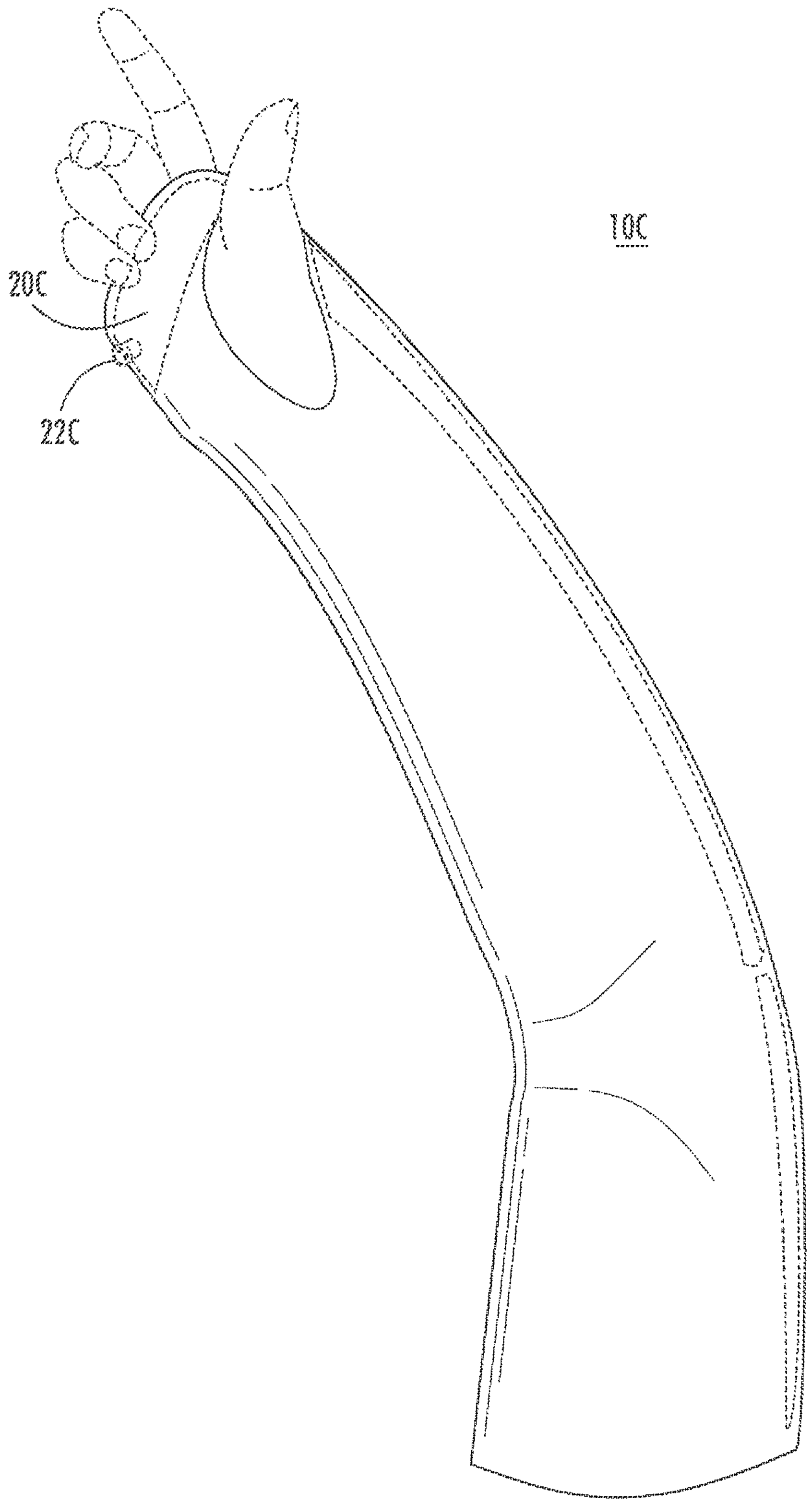
FIG. 9 is a perspective view of the ventral side of a forearm and a hand applied with the inflatable splint of FIG. 8.

In yet another embodiment, referring to FIGS. 7-9, an inflatable splint 10C for a patient's hand and/or forearm includes a sleeve 12C and four separately inflatable chambers: a first chamber 14C surrounding a portion of the dorsal side of a hand, a second chamber 16C surrounding the dorsal side of a lower arm, a third chamber 18C surrounding the dorsal side of an upper arm, and a fourth chamber 20C surrounding the palmar side of the hand.

The embodiment shown in FIGS. 5-6 and 7-9 are the same, excepting the contour and position of a plurality of inflated air chambers which together define a different position and/or orientation for the elbow. More specifically, FIGS. 5-6 show an inflatable splint 10B holding an elbow at an approximately right angle, and FIGS. 7-8 show an inflatable splint 10C holding an elbow at a more extended angle, The plurality of lengthwise-extending tubular chambers in splint 10A, 10B and 10C can be positioned and/or orientated such that an arm pulse checking point is accessible, as shown in FIG. 7.

Figure 10:
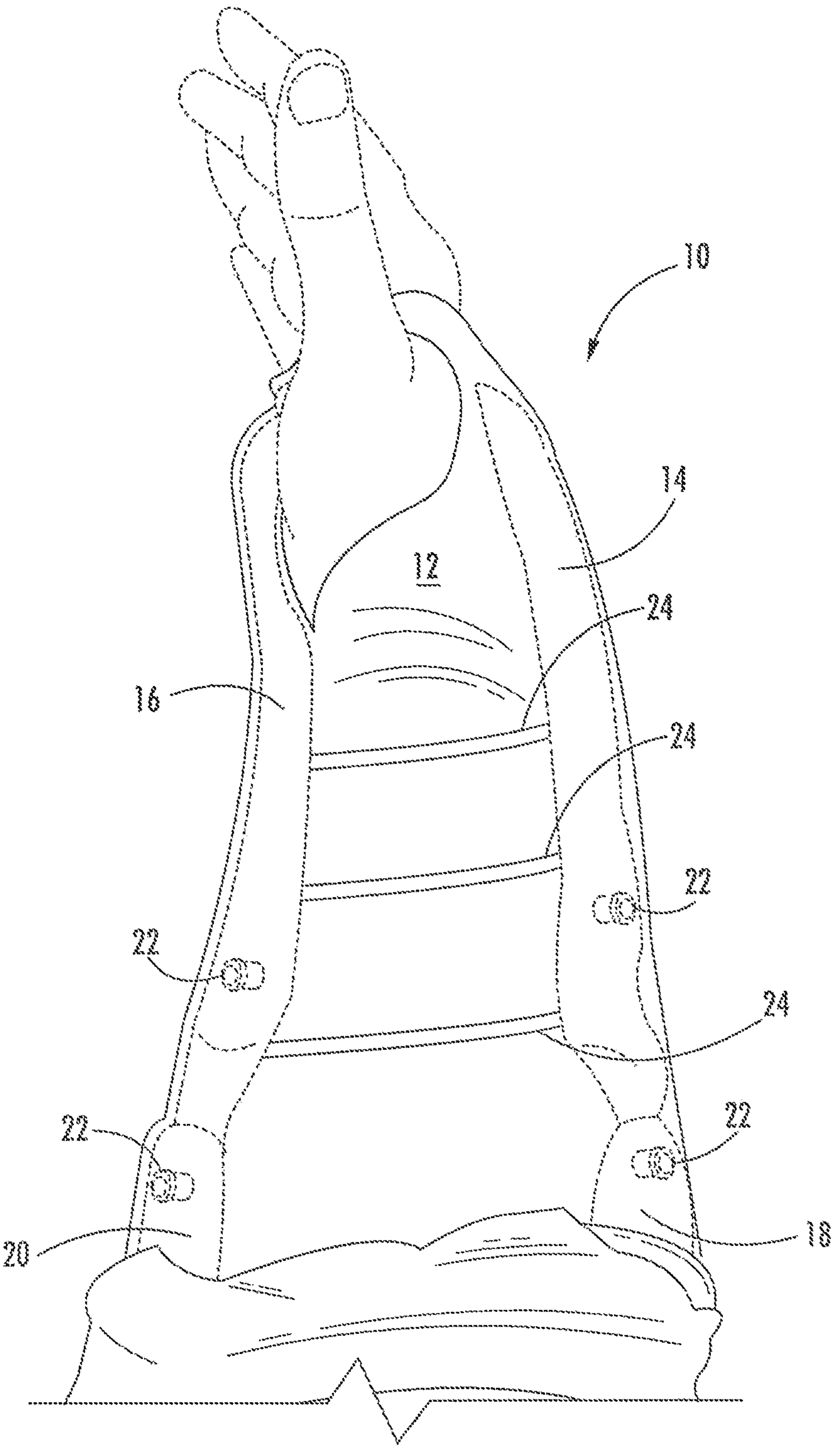
FIG. 10 is a perspective side view of the inflatable splint of FIG. 1 with extra straps to secure the splint in place.

The additional straps 24 can be further adjusted to fit the dimension of a limb and/or joint. Referring to FIG. 10, a plurality of annular straps 24 connecting air chambers can be connected to the suitable portions of the air chambers to secure the splint 10 in the desired position and/or orientation.

Figure 11:
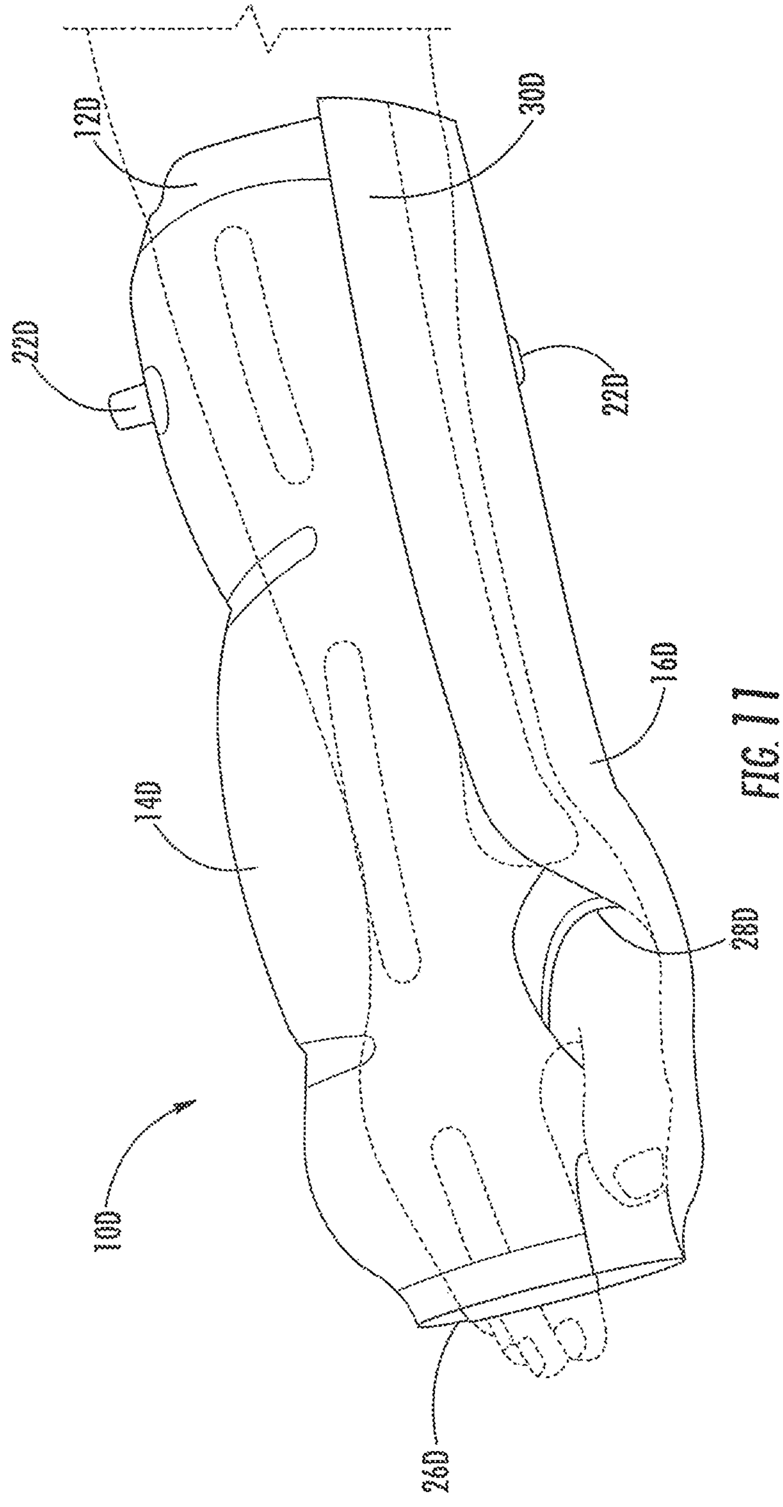
FIG. 11 is a perspective side view of an inflatable splint applied to a hand and a forearm, according to another embodiment of the present invention.

Referring to FIG. 11, a splint 10D includes a sleeve 12D shaped to conform to a portion of a hand and a lower arm. A plurality of chambers includes a chamber 14D surrounding at least a portion of a dorsal side of the hand and a dorsal side of the lower arm, a chamber 16D surrounding at least a portion of a palmar side of the hand and a palmar side of the lower arm. The splint 10D has an open lower end 26D to expose four fingers and allow airflow into the splint 10D. The splint 10D also has an opening 28D for a thumb to pass through. The chamber 14D and the chamber 16D each includes a valve 22D for introducing air into the respective chamber. In the depicted embodiment, the sleeve 12D is formed from a sheet that has hooks and fasteners 30D attached along the longitudinal edge of the sheet to wrap the sheet into a tubular configuration. Example hooks and fasteners include Velcro fasteners or other suitable fasteners. Velcro fasteners can be welded by applying radio frequency (RF) radiation or sewn to the sheet.

Figure 12:
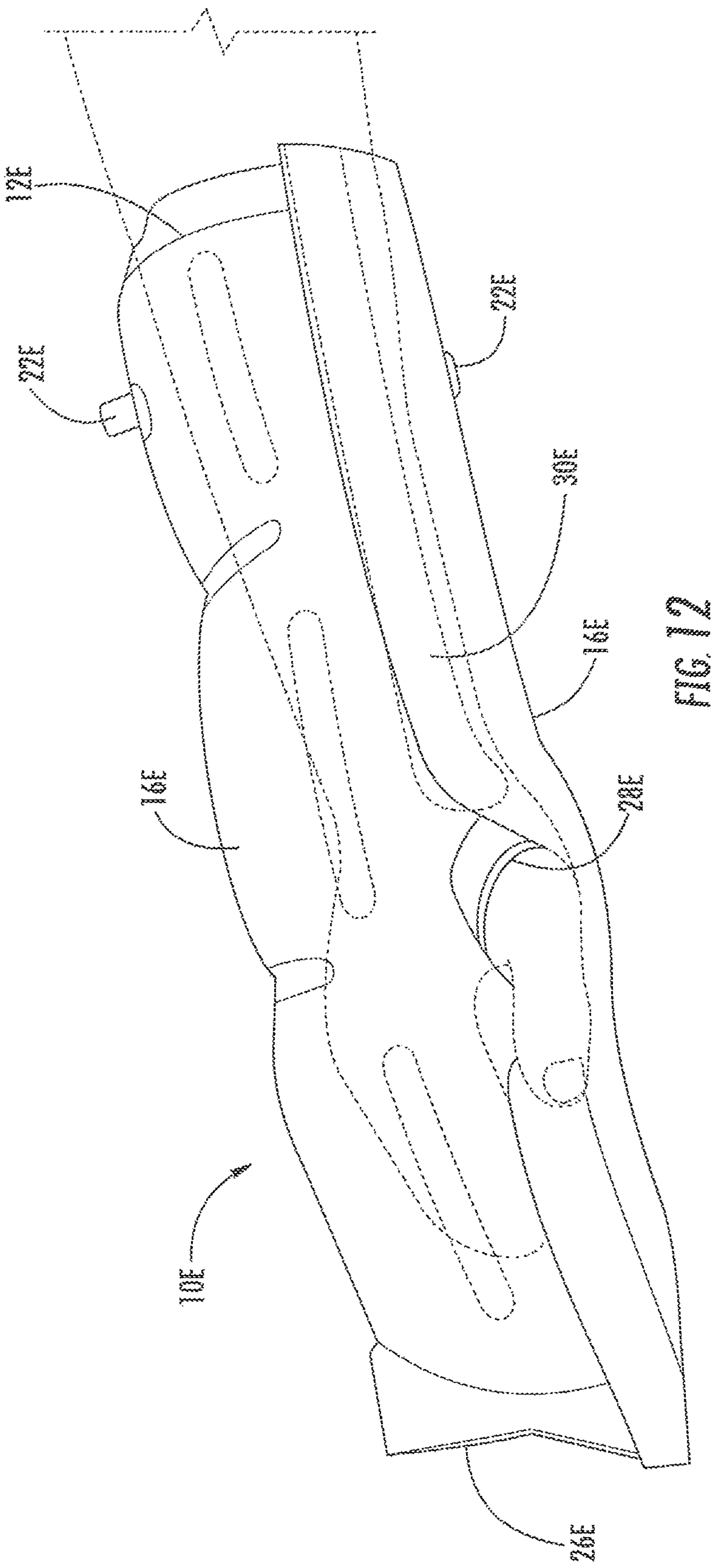
FIG. 12 is a perspective side view of an inflatable splint applied to a hand and a forearm, according to another embodiment of the present invention.

Referring to FIG. 12, according to another embodiment of the present invention, splint 10E is similar to splint 10D except that splint 10E has a closed lower end 26E rather than an opening 26D to expose four fingers.

Figure 13:
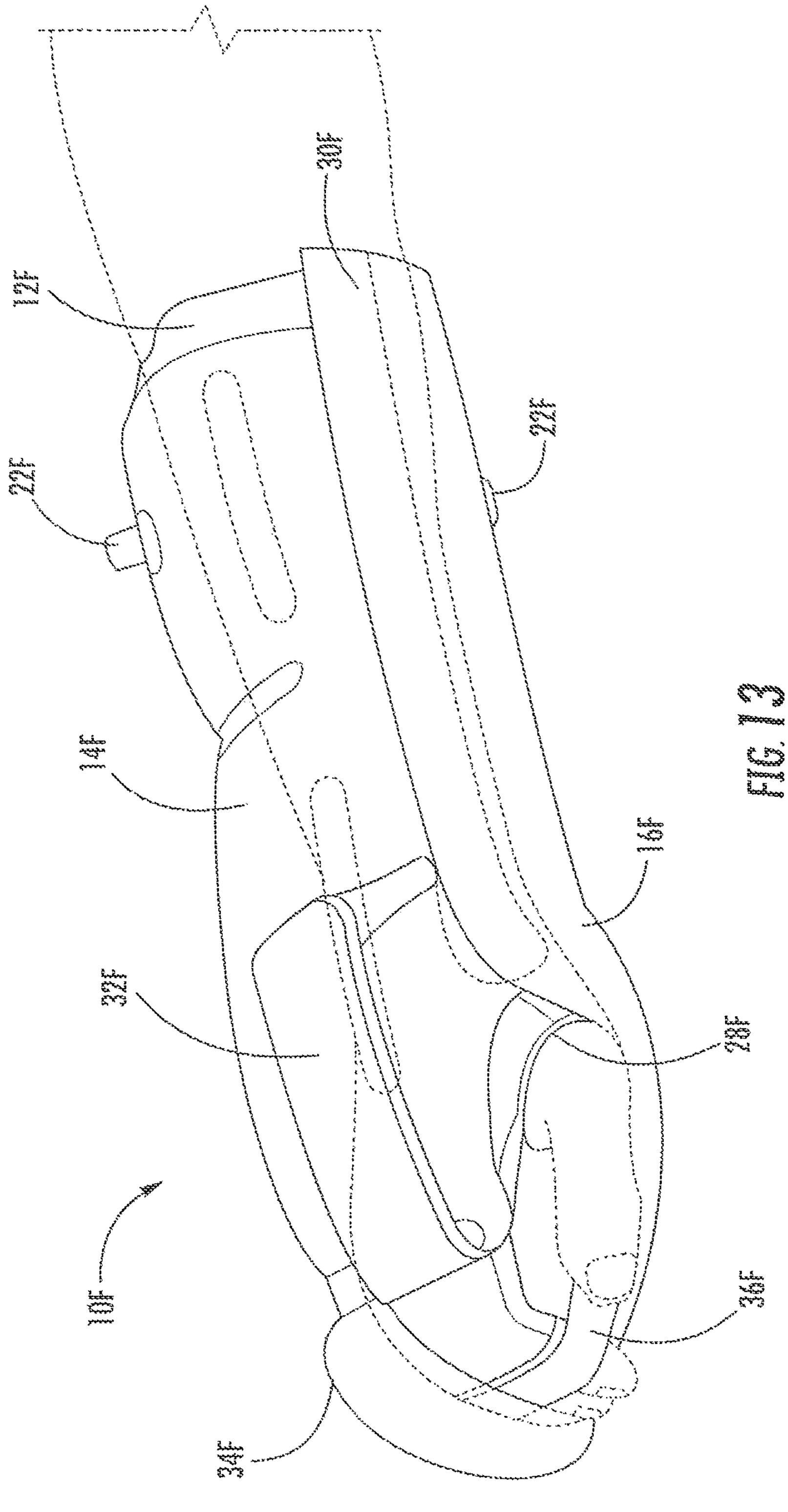
FIG. 13 is a perspective side view of an inflatable splint applied to a hand and a forearm, according to another embodiment of the present invention.

Referring to FIG. 13, according to another embodiment of the present invention, the splint 10F includes four chambers: a chamber 14F surrounding a portion of a dorsal side of the hand and the portion of the arm, a chamber 16F surrounding a portion of a palmar side of the hand and a portion of the arm, a chamber 32F surrounding dorsal side of index finger and middle finger, and a chamber 34F surrounding dorsal side of ring finger and little finger. The chambers 32F and 34F are separately inflatable. In the depicted embodiment of FIG. 13, the chamber 34F can be inflated to hold the ring finger and the little finger in a desired position (e.g., half curled position). The chamber 32F can also be deflated and strapped backwards to keep the corresponding fingers outside the splint 10F. The splint 10F can also have at least one finger strap 36F to hold specific fingers (e.g., the index finger and middle finger) in a bent position.

Figure 14:
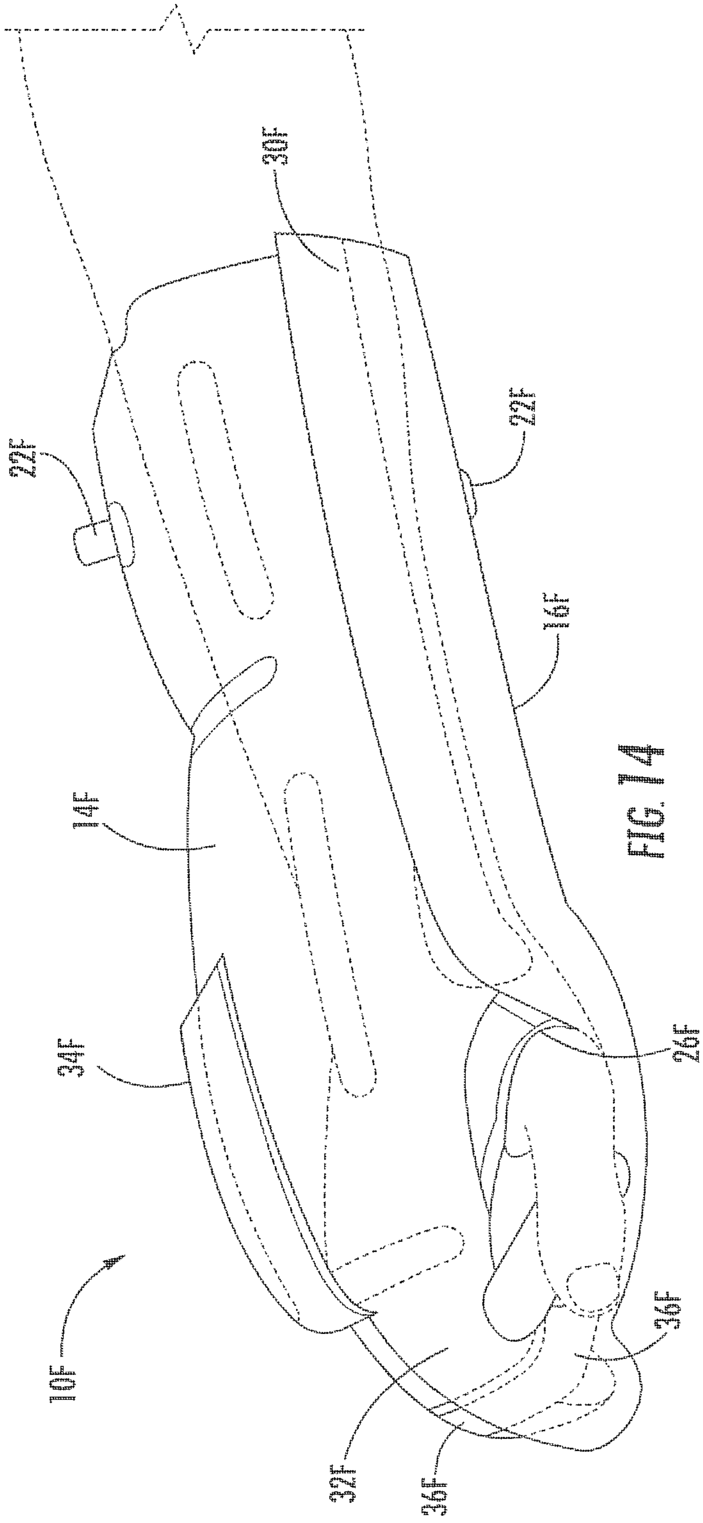
FIG. 14 is another perspective side view of the inflatable splint of FIG. 13 applied to a hand and a forearm.

Referring to FIG. 14, the chamber 32F of the splint 10F is inflated to keep the corresponding fingers (e.g., index finger and middle finger) in a desired position (e.g., half curled position), whereas the chamber 34F is deflated and strapped backward to give certain freedom to the corresponding fingers (e.g., ring finger and little finger) and keep them outside the splint 10F. One or more straps 36F can also be used to keep certain fingers in a bend position.

Figure 15:
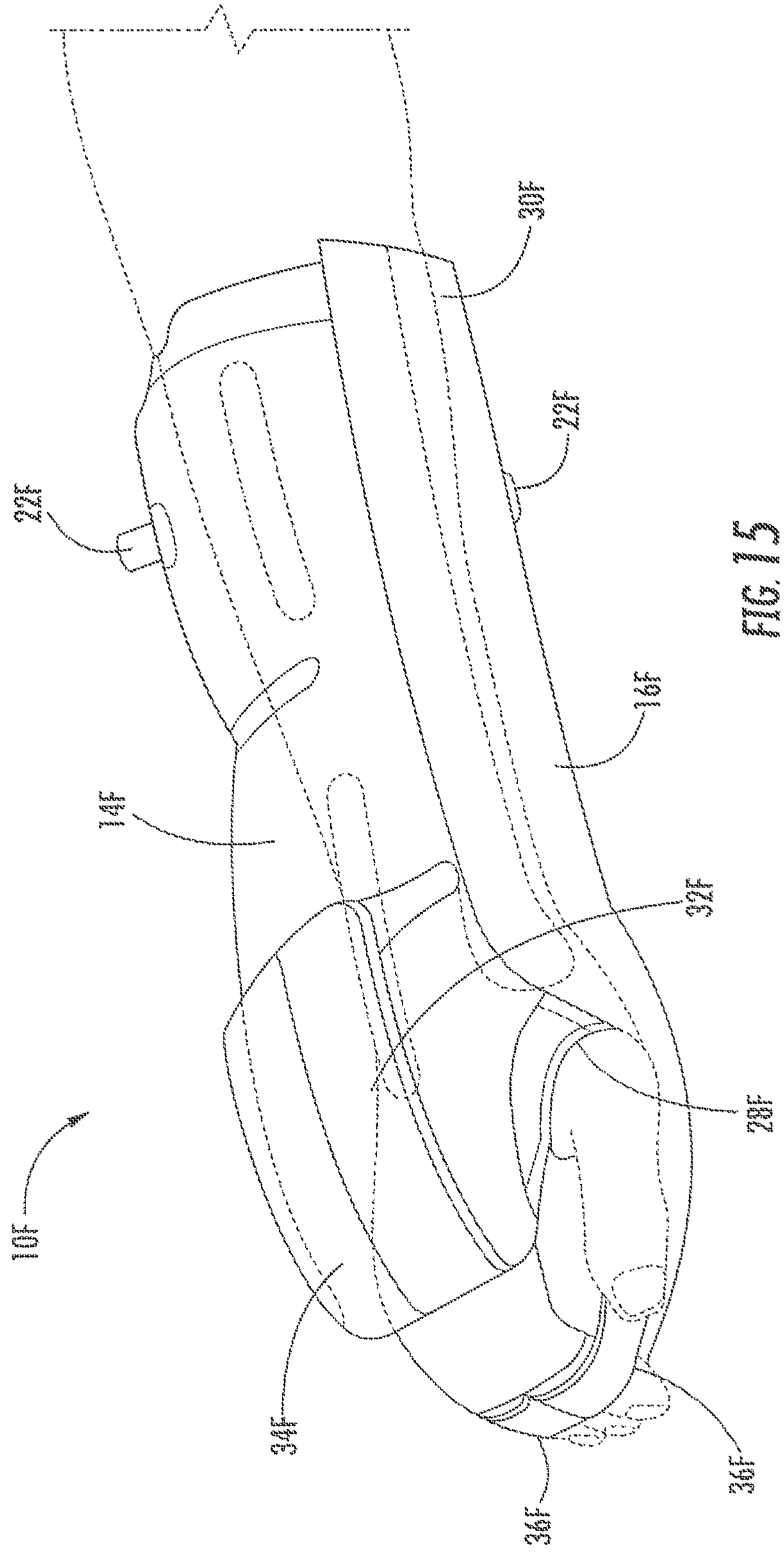
FIG. 15 is another perspective side view of the inflatable splint of FIG. 13 applied to a hand and a forearm, according to another embodiment of the present invention.

Referring to FIG. 15, both chamber 32F and 34F of the splint 10F are deflated and strapped backward to keep four fingers outside the splint 10F. One or more finger straps 36F are used to hold specific fingers in a desired position (e.g., bend position). In the depicted embodiment, one finger strap is used to hold the index finger and middle finger in a bent position, and another finger strap is used to hold the ring finger and little finger in a bent position. Alternatively, the four fingers can be left unstrapped for range of motion activities and functional activities, while still protecting the injured body part (e.g., wrist).

Figure 16:
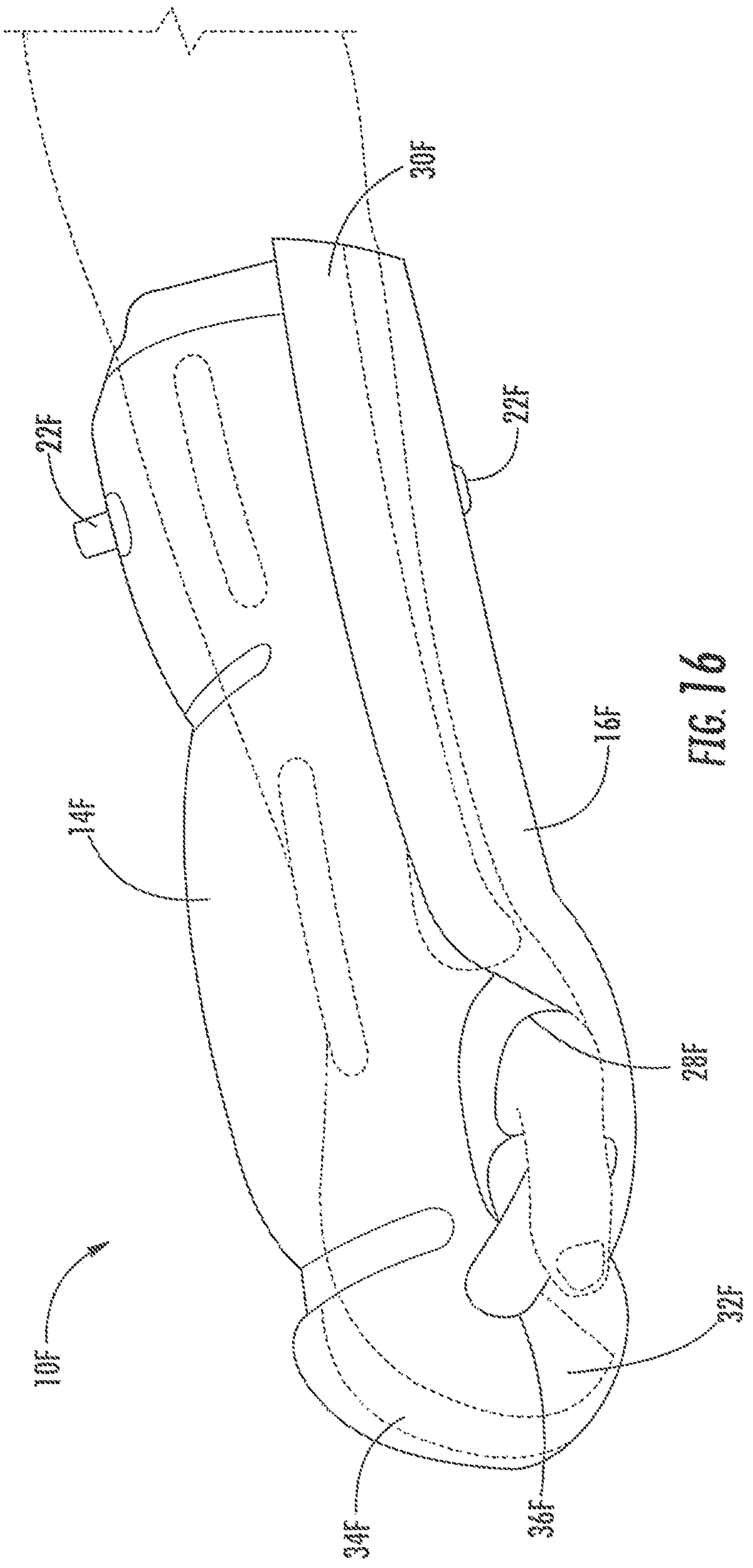
FIG. 16 is a perspective side view of the inflatable splint of FIG. 13 applied to a hand and a forearm, according to another embodiment of the present invention.

Referring to FIG. 16, both the chambers 32F and 34F of the splint 10F are inflated to keep the four fingers in a desired position (e.g., a functional position). In this case, one or more straps 36F can be attached to exterior of the chambers 32F and 34F to keep the chamber in a desired position.

Figure 17:
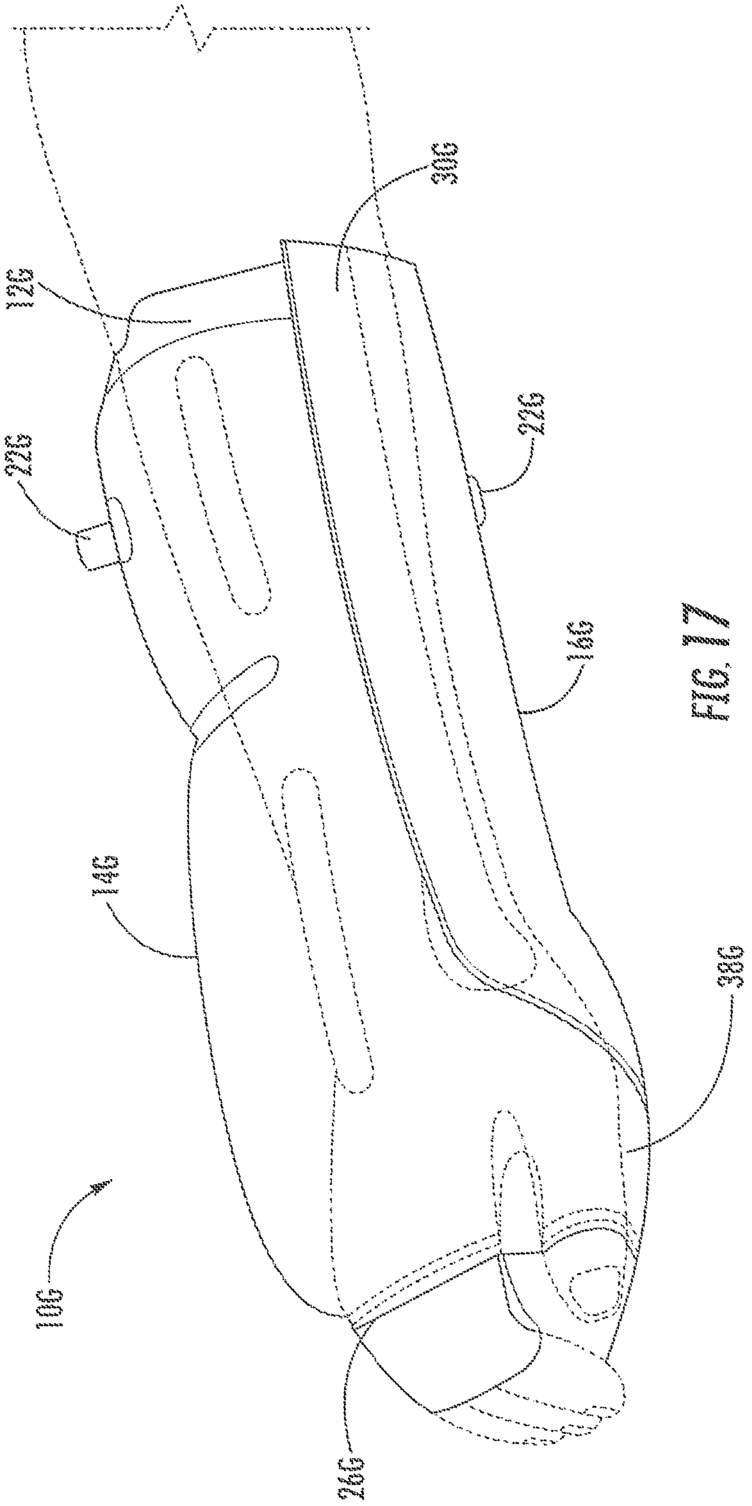
FIG. 17 is a perspective side view of an inflatable splint applied to a hand and a forearm, according to another embodiment of the present invention.

Referring to FIG. 17, according to another embodiment of the present invention, the splint 10G includes a chamber 14G surrounding a portion of the dorsal side of the hand and a portion of the arm, a chamber 16G surrounding a portion of the palmar side of the hand a portion of the arm, and a chamber 38G surrounding the thumb in the splint 10G. The inflated thumb chamber 38G can position the thumb in a desired position.

Figure 18:
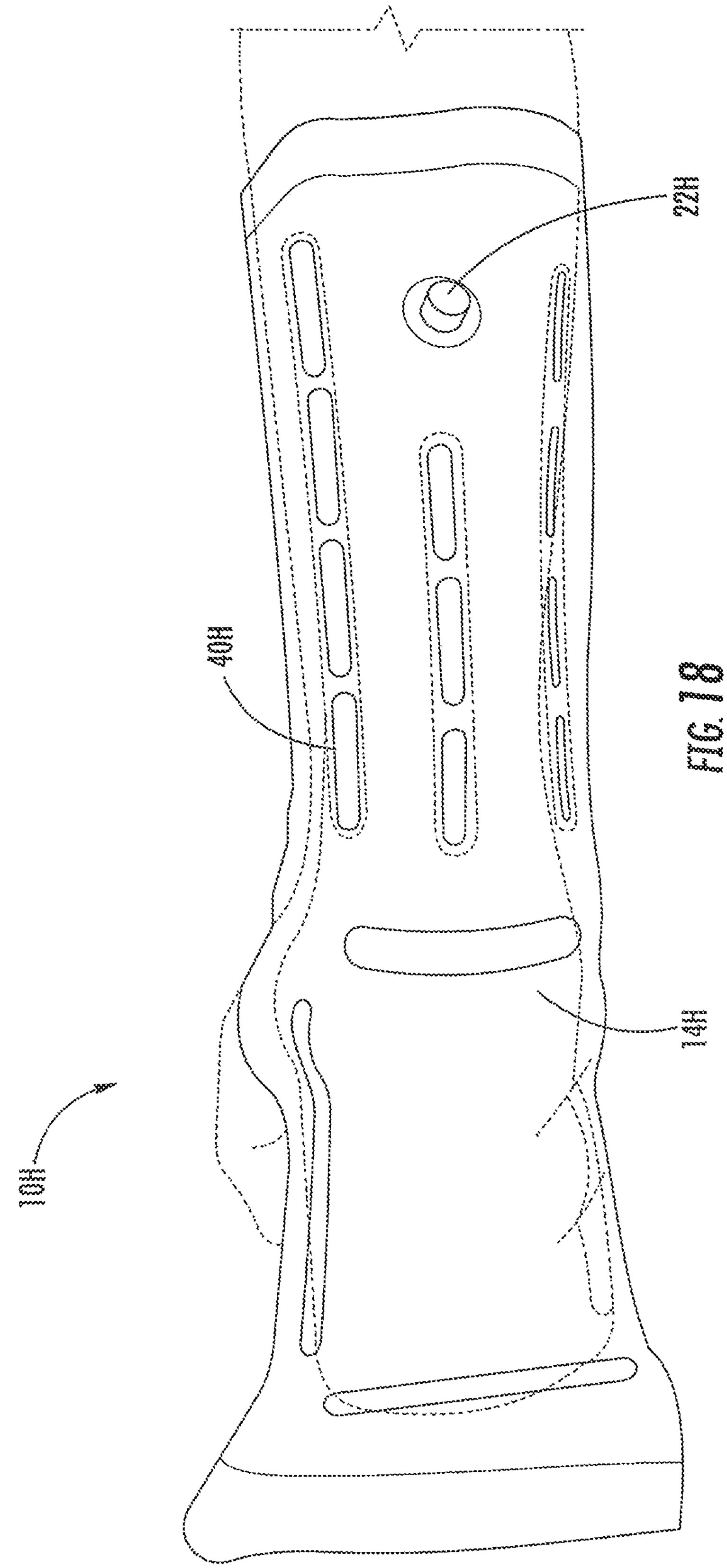
FIG. 18 is a perspective top view of an inflatable splint applied to a hand and a forearm, according to another embodiment of the present invention.

Referring to FIG. 18, according to another embodiment of the present invention, the splint 10H further includes a plurality of vent holes 40H in the sleeve 12H to allow airflow.

Figure 19:
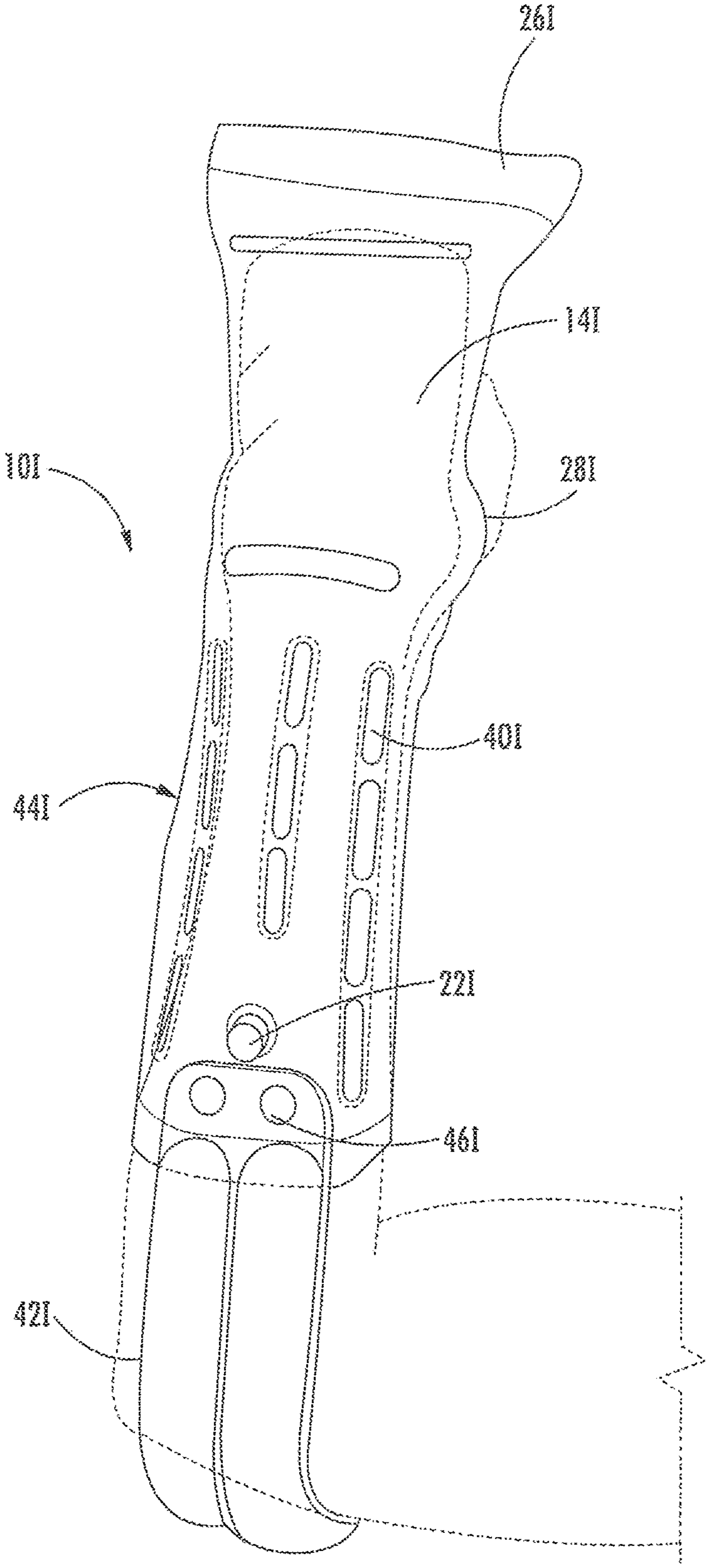
FIG. 19 is a perspective top view of an inflatable splint applied to a hand and a forearm, according to another embodiment of the present invention.

Referring to FIG. 19, the splint 10I further includes an elbow portion 421 releasably attached to a forearm portion 441. For example, the elbow portion 421 can be connected to the forearm portion 441 via snap buttons 461 or other suitable means. The elbow portion 421 can hold a patient's elbow and forearm at relative orientation.

Figure 20:
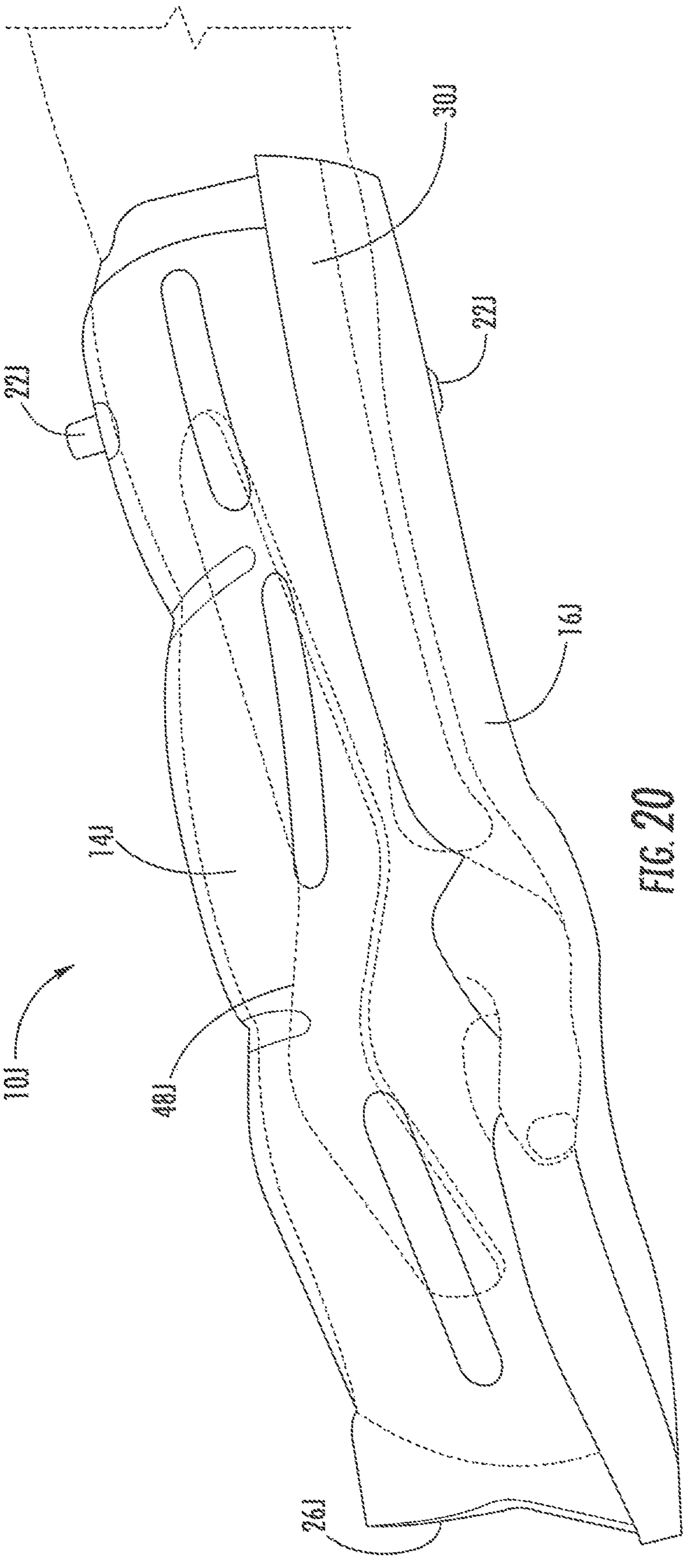
FIG. 20 is a perspective side view of an inflatable splint applied to a hand and a forearm, according to another embodiment of the present invention.

Referring to FIG. 20, according to another embodiment of the present invention, the splint 10J can include a rigid frame 48J covered by the sleeve 12J. The rigid frame 48J is used to hold a hand in a specific position. In the depicted embodiment, the rigid frame 48J is positioned on the dorsal side of the hand. One or more rigid frames can also be positioned on the palmer side of the hand or other appropriate position relative to a suitable body part.

Figure 24:
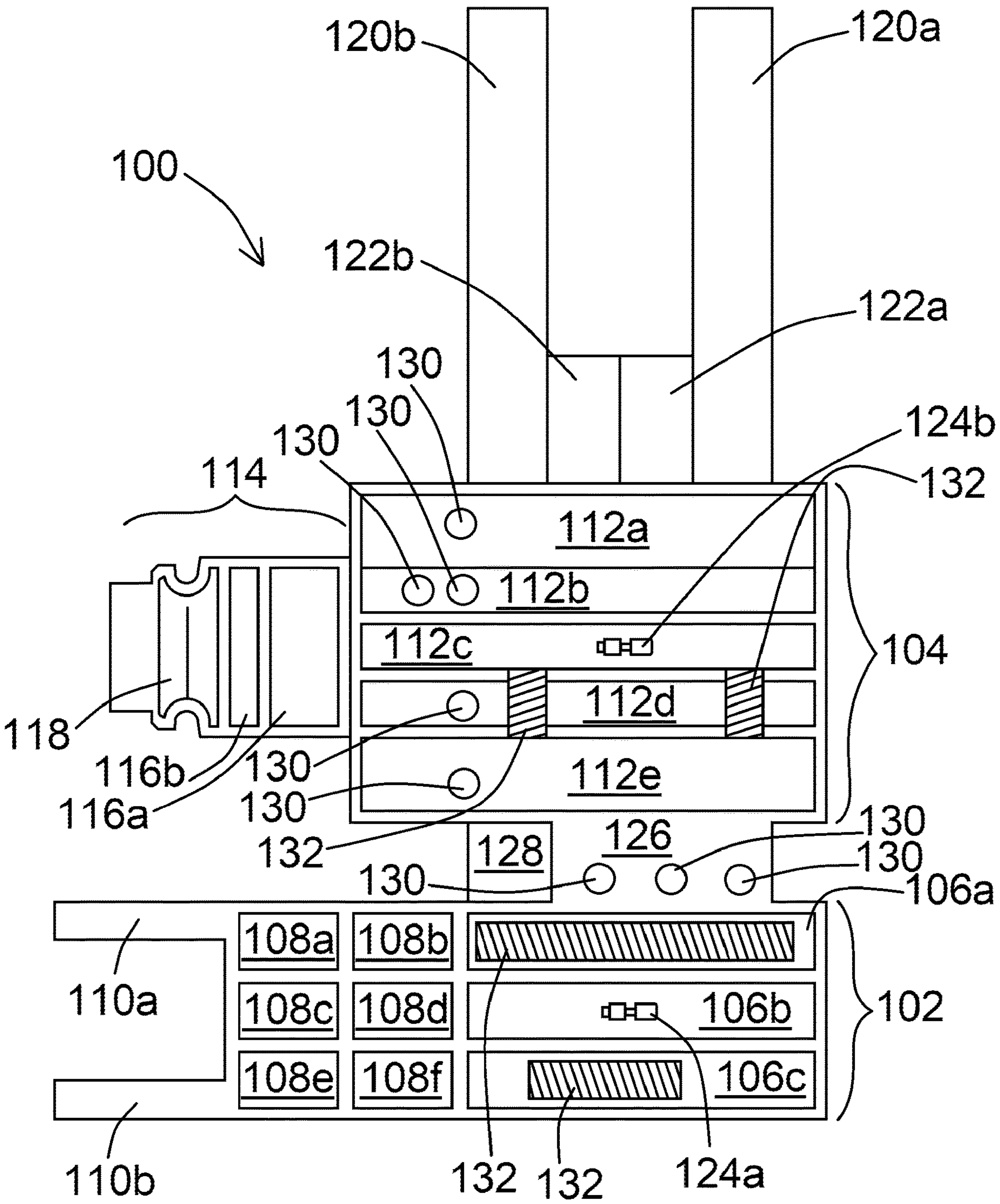
FIG. 24 is an external view of an embodiment of a splint, according to an exemplary embodiment of the present disclosure.

The present disclosure includes disclosure of additional embodiments of splints as referenced herein. As shown in FIG. 24, for example, an outside view of an exemplary splint 100 of the present disclosure is shown, comprising a dorsal portion 102 and a volar portion 104. Dorsal portion 102 can comprise one or more elongated dorsal arm chambers **106*a*, 106*b*, 106*c*, or more, such as two or more, with the plurality of dorsal arm chambers 106*a*, 106*b*, 106*c* being generally parallel to one another. Said dorsal arm chambers 106*a*, 106*b*, 106*c*, when splint 100 is worn by a user on his or her arm, would align with the dorsal side of the forearm. Dorsal portions 102 of exemplary splints 100 of the present disclosure can also comprise one or more dorsal hand chambers, such as first dorsal hand chamber 108*a*, second dorsal hand chamber 108*b*, third dorsal hand chamber 108*c*, fourth dorsal hand chamber 108*d*, fifth dorsal hand chamber 108*e*, sixth dorsal hand chamber 108*f*, or more. Said dorsal hand chambers 108*a*, 108*b*, 108*c*, 108*d*, 108*e* 108*f*, when splint 100 is worn by a user on his or her arm, would align with the dorsal side of the hand (the general "back" of the hand). There are two effective sets of dorsal hand chambers in series, namely dorsal hand chambers 108*a*, 108*c*, 108*e* to support the back of the fingers of the hand, and dorsal hand chambers 108*b*, 108*d*, 108*f* to support the back of the hand. Dorsal portions 102 may also have one or more finger straps 110*a*, 110*b*, or more, extending therefrom, said finger straps 110*a*, 110*b* used to secure the splint 100 in place when worn. Finger straps 110*a*, 110*b*, when a user is wearing such a splint 100 embodiment, would attach back to parts of the splint 100** on the volar side so that the user's fingers are held in a flexed position.

Splints 100 of the present disclosure can also comprise a volar portion 104, such as shown in FIG. 24 and noted above. Volar portion 104 can comprise one or more elongated volar arm chambers **112*a*, 112*b*, 112*c*, 112*d*, or more, such as two or more. Said volar arm chambers 112*a*, 112*b*, 112*c*, 112*d*, when splint 100 is worn by a user on his or her arm, would align with the volar side of the forearm. Volar portions 104 of exemplary splints 100 of the present disclosure can also comprise a palm portion 114 extending longitudinally therefrom, palm portion 114 having one or more palm chambers, such as first palm chamber 116*a*, second palm chamber 116*b*, or more. Exemplary splints 100 of the present disclosure may also comprise a distal palm chamber 118, such as shown in FIG. 24. Said palm chambers 116*a*, 116*b*, 118, when splint 100 is worn by a user on his or her arm, would align with the palm of the hand. In at least some embodiments, palm chambers 116*a*, 116*b* and distal palm chamber 118 are in series with the various volar arm chambers and are inflated using valve 124***b*, as noted in further detail herein.

Splints 100 of the present disclosure can also comprise a first forearm stabilization strap 120*a*, a second forearm stabilization strap 120*b*, or more, a first dorsal elongation strap 122*a*, a second dorsal elongation strap 122*b*, or more, extending perpendicularly from volar portion 104. Said forearm stabilization straps 120*a*, 120*b* can be used to secure the splint 100 in place when worn, going around the splint 100 and attaching back to themselves, while said dorsal elongation straps 122*a*, 122*b* can smooth out forces between the dorsal and volar sides of the splint 100 when connected to hook and loop fastener portions 130 or 132, as referenced in further detail herein.

The various chambers referenced herein can be inflated using an inflation tool via one or more valves 124*a*, 124*b*, or more, positioned within at least one of the chambers. For example, and as shown in FIG. 24, valve 124*a* can be used to inflate dorsal arm chambers 106*a*, 106*b*, and 106*c*, along with dorsal hand chambers 108*a*, 108*b*, 108*c*, 108*d*, 108*e*, and 108*f*, as said chambers are in communication with one another so that only one valve 124*a* is needed to inflate said chambers. Similarly, a second valve (valve 124*b*) can be used to inflate volar arm chambers 112*a*, 112*b*, 112*c*, and 112*d*, and palm chambers 116*a*, 116*b*, and 118, as said chambers are in communication with one another so that only one valve 124*b* is needed to inflate said chambers. In at least one embodiment, volar arm chambers 112*a*, 112*e* are relatively larger (wider) than volar arm chambers 112*b*, 112*c*, 112*d*, whereby volar arm chambers 112*a*, 112*e* provide lateral forearm support on the volar side, while volar arm chambers 112*b*, 112*c*, 112*d* provide volar support (forearm structural rigidity.

Dorsal portion 102 and volar portion 104 are connected to one another by way of a connection portion 126, such as shown in FIG. 24. Connection portion 126, as well as various other portions of an exemplary splint 100, such as one or more chambers referenced herein, can have a portion of hook and loop fastener 130, 132 adhered thereto, so that when the splint 100 is worn by a user, the portions of hook and loop fastener 130, 132 that contact one another can secure the splint 100 in place as desired. One or more flaps 128 can be used to cover one or more hook and loop fastener portions 130, with said flaps being coupled to or adjacent to connection portion 126.

Figure 25:
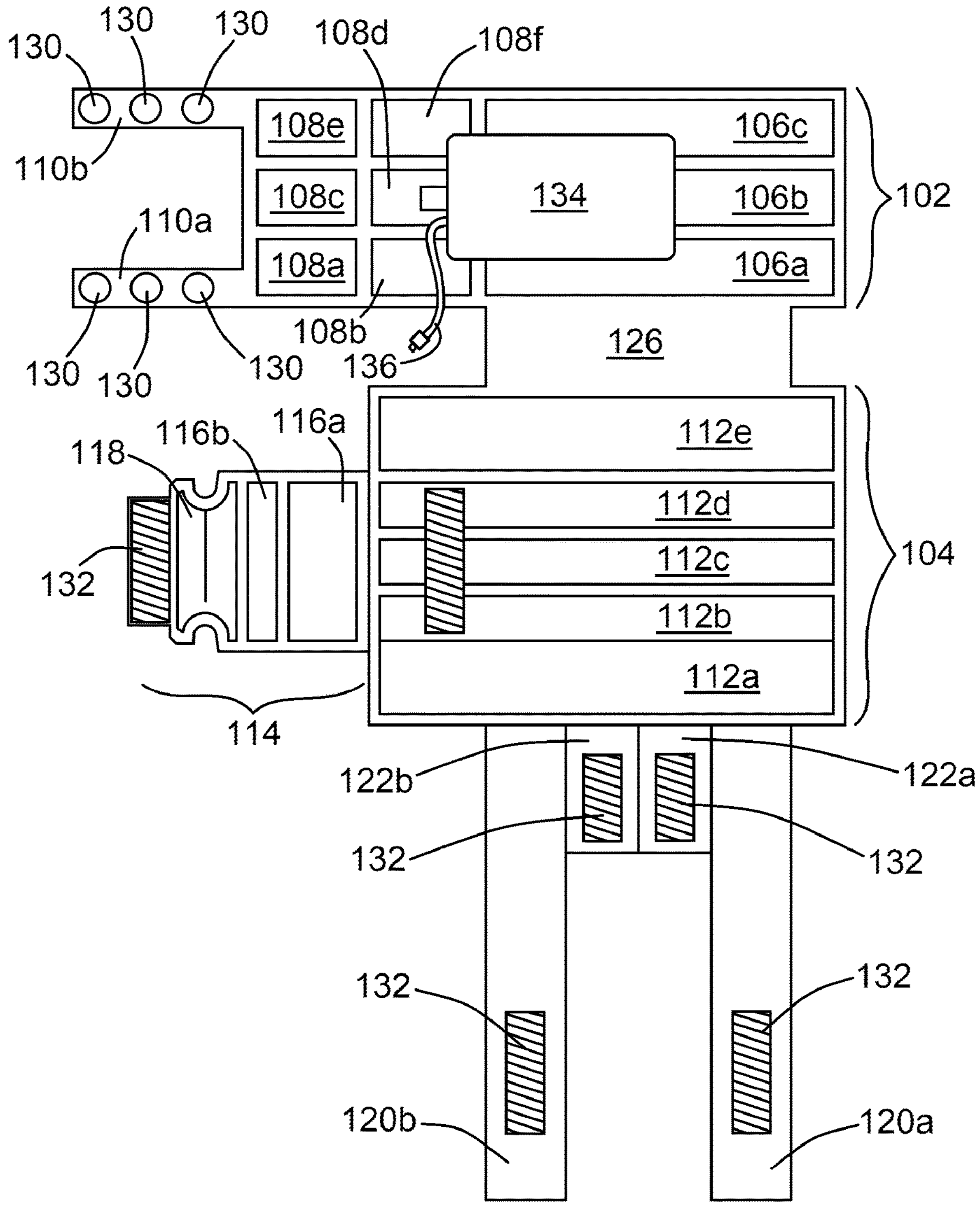
FIG. 25 is an internal view of the embodiment of the splint of FIG. 24.

FIG. 25 shows an inside view of an exemplary splint 100 of the present disclosure. As shown therein, splint 100 comprises the same various chambers as disclosed above, but has hook and loop fastener portions 130, 132 at different locations. A forearm bladder 134, such as shown in FIG. 25, is coupled to the dorsal portion 102 of the splint 100, and can be inflated separately using inflation tube 136. Inflation tube 136 is generally on the outside of splint 100 so that it can be used to inflate forearm bladder 134, which is generally intended to be positioned on the forearm proximal to the wrist crease. Inflation of forearm bladder 134, after the splint has been positioned about an arm of a user and after the other chambers have been inflated, is intended to further stabilize the forearm within said splint 100.

Figure 26:
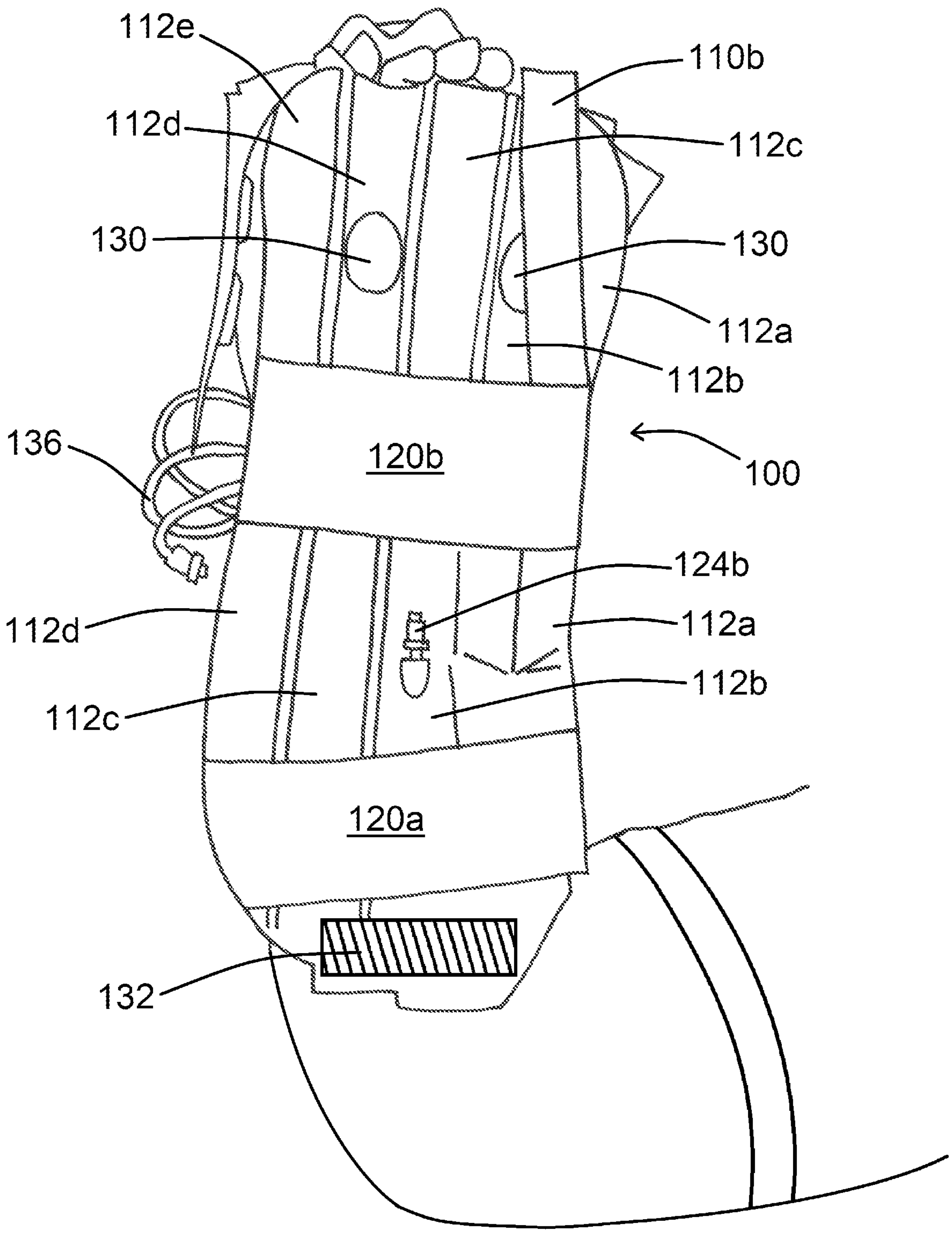
FIG. 26 is a view of a splint of the present disclosure positioned about a forearm of a user to stabilize the forearm.

When splint 100 is worn by a user, the various chambers can be inflated to stabilize splint 100 about the arm and hand of the user, and forearm bladder 134 can be inflated to improve overall comfort and address any lack of comfort due to a forearm being smaller or larger than average and also address concerns that the gap created at the wrist from inflation of the various dorsal arm chambers because the forearm is wider at the elbow and smaller at the wrist. In addition, and as overall arm swelling goes down, the forearm bladder 134 can be further inflated to add structural rigidity to the wrist as the anatomy changes. FIG. 26 shows an exemplary embodiment of a splint 100 of the present disclosure being worn on a forearm and hand of a user, whereby the various chambers are inflated, and whereby straps 120*a*, 120*b* are wrapped around splint 100 to secure splint 100 to the forearm to stabilize the forearm.

Figure 27:
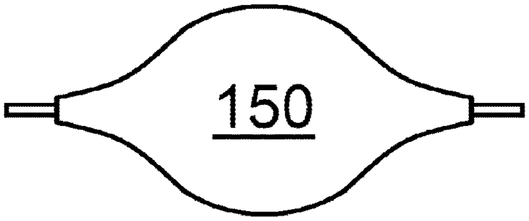
FIG. 27 shows an inflation tool, according to an exemplary embodiment of the present disclosure.

FIG. 27 shows an exemplary inflation tool 160 of the present disclosure. In at least one embodiment, inflation tool 160 is a squeeze-bulb that can attach to a valve 124 or to inflation tube to inflate various portions of a splint 100 of the present disclosure.

Figure 28:
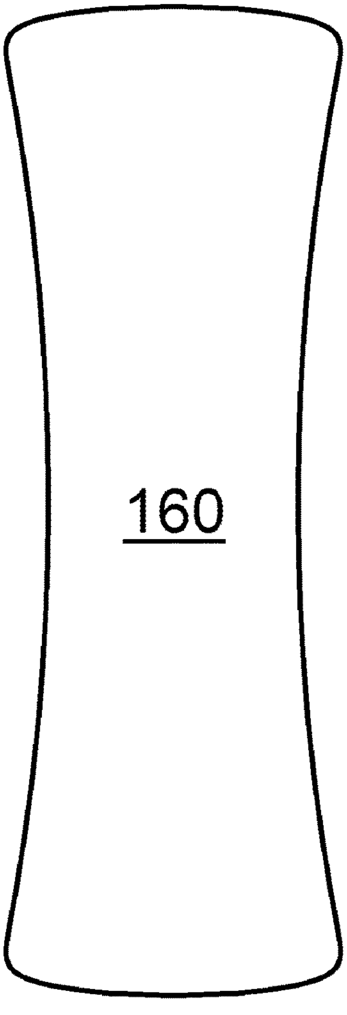
FIG. 28 shows a relative outside of an elbow strap, according to an exemplary embodiment of the present disclosure.
Figure 29:
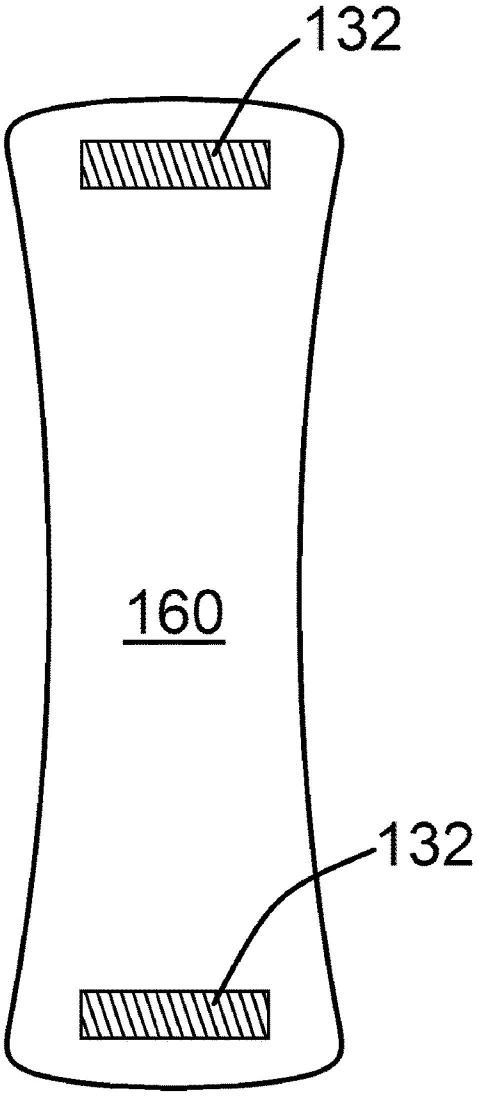
FIG. 29 shows a relative inside of an elbow strap, according to an exemplary embodiment of the present disclosure.

FIG. 28 shows a relative outside, and FIG. 29 shows a relative inside, of an exemplary elbow strap 160 of the present disclosure. As shown therein, an exemplary elbow strap can have hook and loop fastener portions 132 coupled thereto, configured to attach to hook and loop fastener portions 132 on a relative bottom of a splint 100, such as shown in FIG. 26. Elbow strap 160 would attach on one side of a splint 100 (when worn), wrap around the elbow of the user, and attach to the other side of splint 100 so to immobilize the elbow, such as when rotation of the forearm or movement of the elbow relative to the splint 100 needs to be limited.

Figure 30:
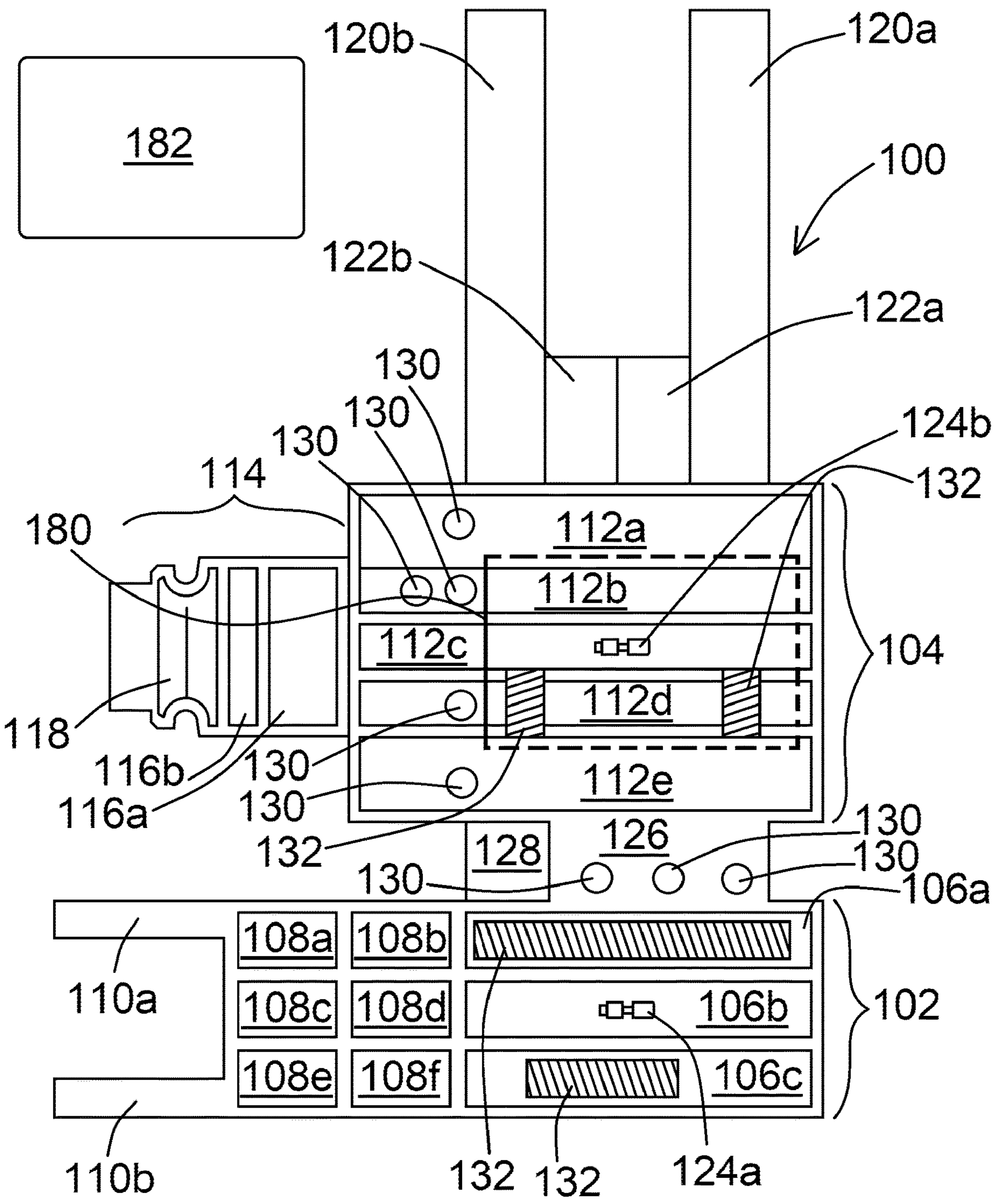
FIG. 30 is an external view of an embodiment of a splint having a pocket, according to an exemplary embodiment of the present disclosure.

FIG. 30 shows a relative outside of an exemplary splint 100 of the present disclosure, such as shown in FIG. 24, but having a pocket 180 defined therein. Pocket 180, as shown in FIG. 30, is configured to receive a cooling pack 182 (such as an ice pack) therein, so to provide potential relief to the user due to swelling of the forearm, for example.

Figure 31:
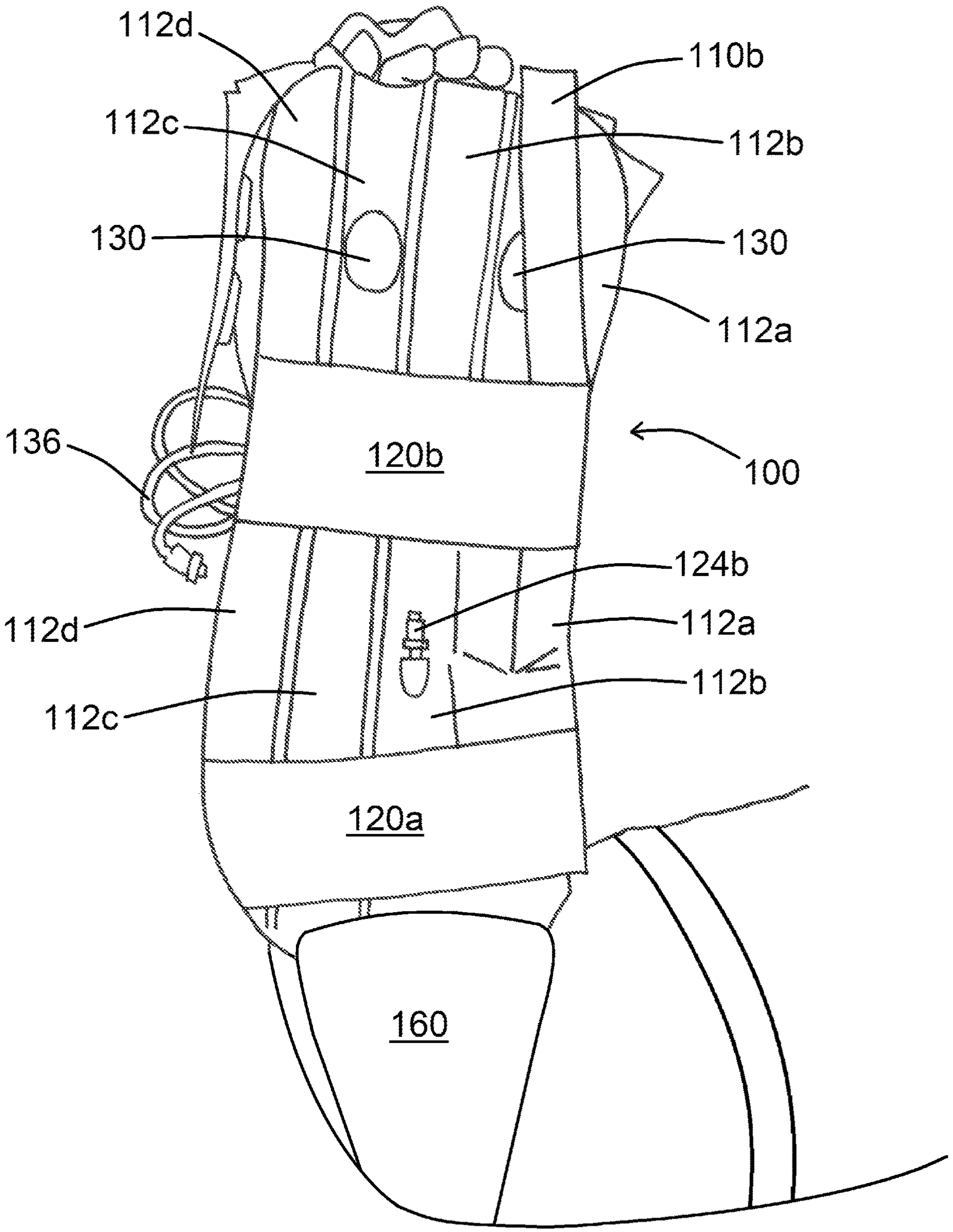
FIG. 31 is a view of a splint of the present disclosure positioned about a forearm of a user to stabilize the forearm and having an elbow strap coupled thereto, according to an exemplary embodiment of the present disclosure.

FIG. 31 shows an exemplary embodiment of a splint 100 of the present disclosure being worn on a forearm and hand of a user, whereby the various chambers are inflated, and whereby straps 120*a*, 120*b* are wrapped around splint 100 to secure splint 100 to the forearm to stabilize the forearm. FIG. 31 also shows an elbow strap 160, as referenced herein, wrapped around an elbow of the user and connected to the dorsal side and the volar side of the splint 100 using hook and loop fastener portions 132. Such an embodiment helps to further stabilize the forearm relative to the elbow.

Figure 32:
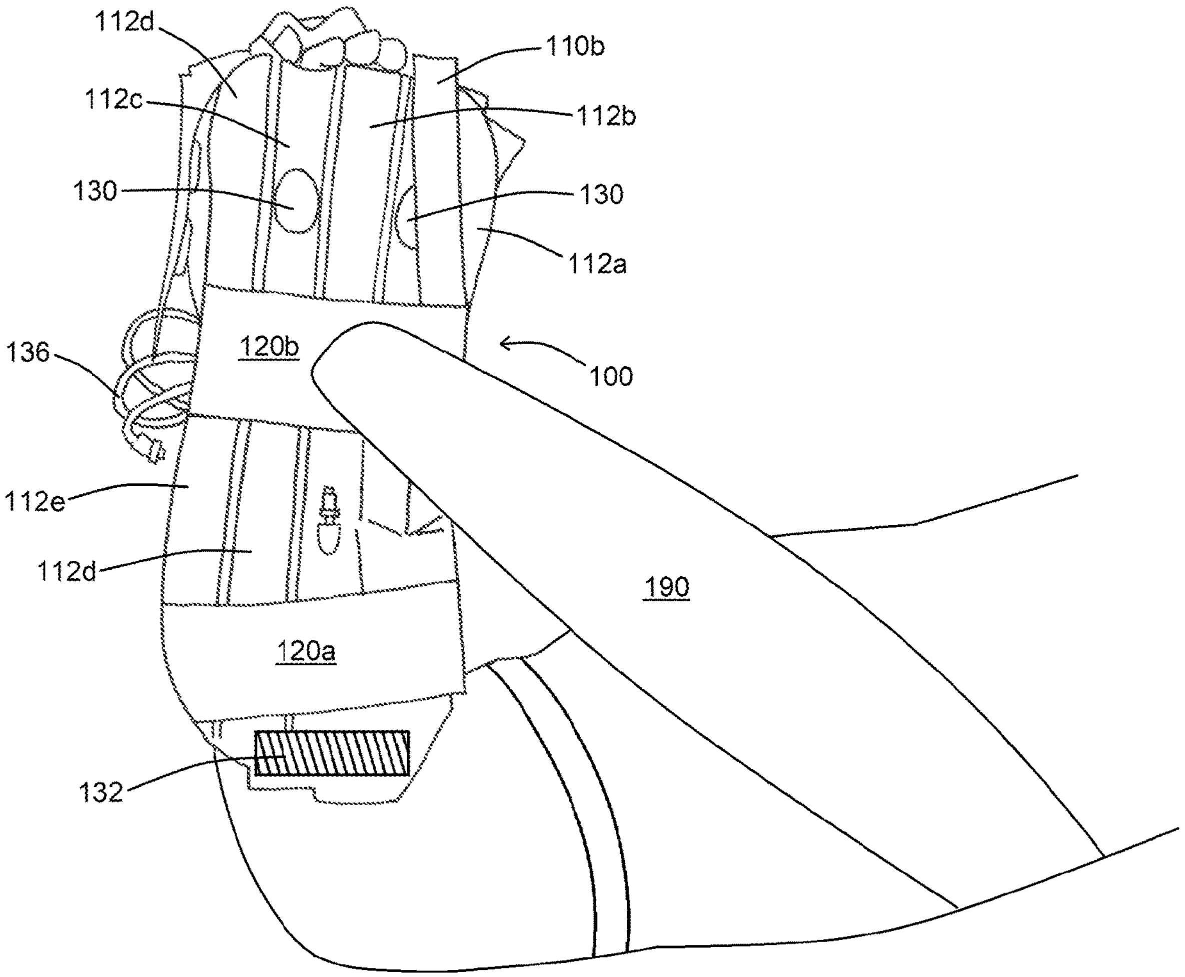
FIG. 32 is a view of a splint of the present disclosure positioned about a forearm of a user to stabilize the forearm having a triceps strap coupled thereto, according to an exemplary embodiment of the present disclosure.

FIG. 32 shows an exemplary embodiment of a splint 100 of the present disclosure being worn on a forearm and hand of a user, and further comprising a triceps strap 190 configured to connect to a volar portion and a dorsal portion of splint 100 using hook and loop fastener portions 132, while wrapping around the upper arm at the triceps. Such an embodiment helps to stabilize the forearm, elbow, and upper arm relative to one another.

The sleeve 12 (and splints 100 generally) can be made of a plastic material treated with an anti bacterial agent. The sleeve material is relatively soft and preferably somewhat elastic so that it can fit well around regions in the vicinity of a limb and/or joint. Nylon is also an exemplary material suitable for splints 100, as nylon does not cause skin irritation, it is comfortable (can be worn for weeks), and is sweat-wicking for additional comfort.

The air chambers can be constructed of any material which lends itself to inflation by air or other compressed gases, such as rubber, rubberized fabric, plastic resins (e.g., polyvinyl chloride, polyethylene and polypropylene) and/or other elastomeric materials. The air chamber wall is of sufficient thickness and elasticity such that desired pressures and tensile forces can be achieved without excessive filling of the air bladder. The plurality of chambers can be made of two-ply material, one-ply material, or a combination thereof.

The inner side of the chamber (the side that is closest to a patient's limb) can be made of a more pliable material than the outer side for a snug fit to the contours of the patient's limb and comfortable and even pressure applied to the patient's limb. The outer side of the air chamber (the side that is farthest away from the patient's limb) can employ a more rigid (e.g., raft-like) material than the inner side to apply a counterforce and control the overall dimension of the splint 10.

In use, a body part (e.g., a limb, a joint, a hand) is admitted into an open-ended sleeve, enabling the rapid and proper positioning, of a plurality of air chambers thereon prior to inflation. One or more of the plurality of air chambers can be inflated to maintain a body part in a desired position and/or orientation. Alternatively, a body part can be first positioned on an open sheet and the sheet can be wrapped into a tubular sleeve and sealed on the longitudinal edge of the sheet.

Figure 21:
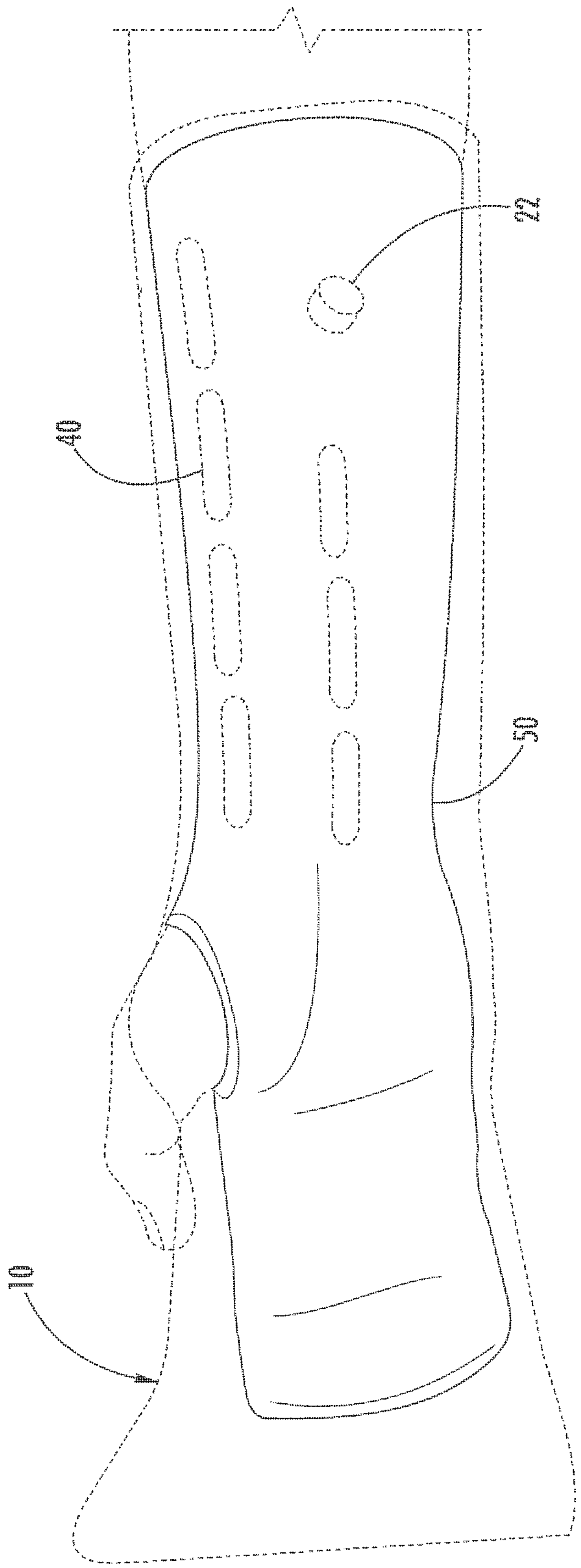
FIG. 21 is a perspective top view of an inflatable splint applied to a hand and a forearm, according to another embodiment of the present invention.

Referring to FIG. 21, according to one embodiment of the present invention, a body part can be covered with a fabric sock 50 before admitted to the sleeve to increase the comfort level of the patient. The fabric sock 50 can also be cleaned easily.

The disclosed splint can be secured into place via a variety of methods. For example, the air chambers of the splint are compressive enough to hold the splint 10 in place once inflated, as shown, for example, in. FIGS. 1-8 and 11-20.

Figure 22:
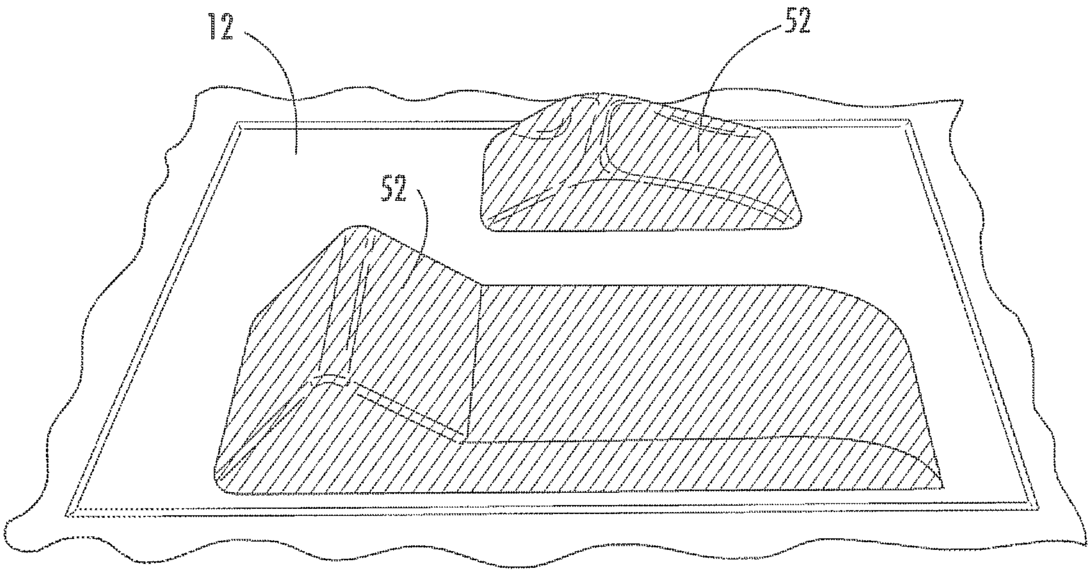
FIG. 22 is a perspective view of a plurality of molds positioning on a sheet for forming a plurality of air chambers, according to another embodiment of the present invention.
Figure 23:
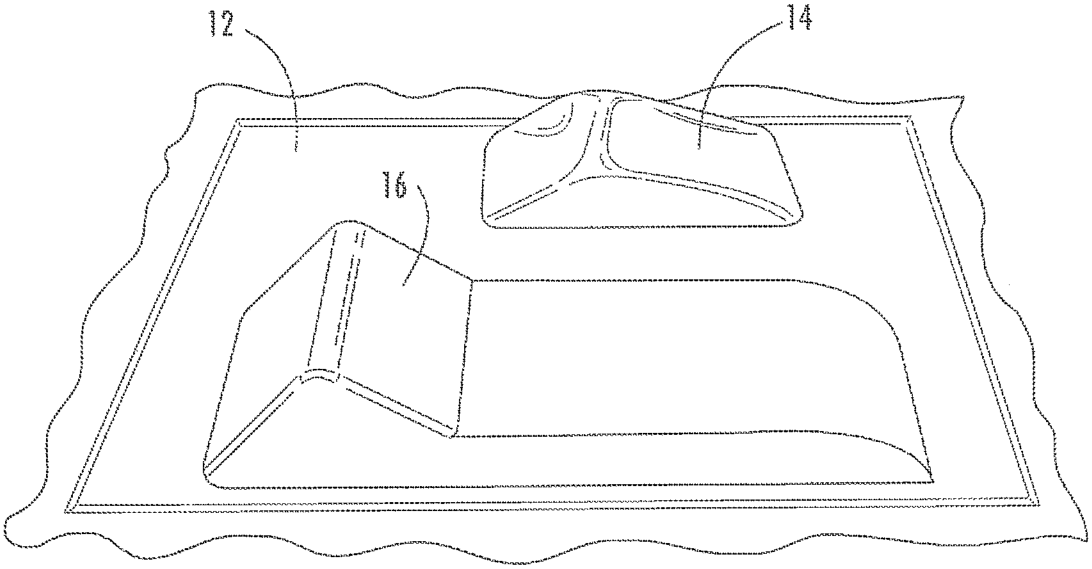
FIG. 23 is a perspective view of air chambers formed on the sheet of FIG. 22, according to another embodiment of the present invention.

Referring to FIGS. 22 and 23, the disclosed inflatable splint can be made by first determining locations of a plurality of air chambers on a sheet 12 and positioning respective molds 52 of predetermined dimension on the determined locations. A plurality of air chambers (e.g., chamber 14, chamber 16) are formed on the sheet according to the respective molds at the determined locations by, for example, RF bonding. One or more loops and fasteners (not shown) on at least one longitude edge of the sheet.

The splint of this invention can be quickly and properly positioned on a limb without causing any added discomfort or pain to the wearer. The highly flexible character of the splint enables it to be readily applied in a natural, conforming position even on such angular areas of the body as the juncture of the foot and ankle. The application of the splint does not require a person with previous experience with applying splints.

The splint of this invention allows an untrained team member to apply the splint to deliver an injured patient in comfort from the emergency care setting to a specialist, even if that visit is delayed for several days to one or more weeks. The splint can maintain the specific human body part in a specific predetermined position that preserves the long term functional position of the limb for the duration of the splinting process. As such, the splint can prevent further damage to the injured limb due to incorrect splint positioning and excessive tightness or pressure from the splint.

After deflation, the splint can be easily folded into a compact package for convenient carrying and storage such as a first aid kit. The uniquely simple construction of the splint, furthermore, enables it to be manufactured at minimal cost with conventional equipment from readily available materials. The inflatable splint is lightweight and therefore allows a user to move the body part inside the splint freely as a whole.

From the foregoing, it will be appreciated that an inflatable splint according to the present invention includes several easily constructed components which can be quickly adapted to conform a body part to an intended position or orientation. The inflatable splint can also be quickly and easily deflated and removed from the body part when it is not needed.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described and the claims appended hereto.

The invention claimed is:

1. An inflatable splint comprising:
- a volar portion comprising a plurality of volar arm chambers, each parallel to one another;
- a dorsal portion comprising a plurality of dorsal arm chambers, each parallel to one another;
- a plurality of hand chambers adjacent the plurality of dorsal arm chambers; and
- a first forearm stabilization strap extending from the dorsal portion and configured to wrap around the splint when the splint is worn by a user.

2. The inflatable splint of claim 1, wherein when the splint is worn by a user and when wherein each dorsal arm chamber of the plurality of dorsal arm chambers are inflated, a lengthwise dorsal portion of a forearm is stabilized by the splint.

3. The inflatable splint of claim 2, wherein a first dorsal valve is configured to inflate each of the dorsal arm chambers of the plurality of dorsal arm chambers.

4. The inflatable splint of claim 3, wherein when the splint is worn by a user and when each of the plurality of hand chambers are inflated, a back of a hand of the user is stabilized by the splint.

5. The inflatable splint of claim 4, wherein the first dorsal valve is further configured to inflate the plurality of hand chambers.

6. The inflatable splint of claim 1, further comprising:
- a plurality of hook and loop fastener portions positioned upon the splint.

7. The inflatable splint of claim 6, wherein the first forearm stabilization strap is configured to wrap around the splint when the splint is worn by a user and to be secured to the splint using at least one hook and loop fastener portion of the hook and loop fastener portions.

8. The inflatable splint of claim 7, further comprising:
- a second forearm stabilization strap extending from the dorsal portion and configured to wrap around the splint when the splint is worn by a user.

9. The inflatable splint of claim 8, wherein the second forearm stabilization strap is configured to wrap around the splint when the splint is worn by a user and to be secured to the splint using at least one hook and loop fastener portion of the hook and loop fastener portions.

10. The inflatable splint of claim 1, wherein when the splint is worn by a user and when each volar arm chamber of the plurality of volar arm chambers are inflated, a lengthwise volar portion of a forearm is stabilized by the splint.

11. The inflatable splint of claim 10, wherein a first volar valve is configured to inflate each of the volar arm chambers of the plurality of volar arm chambers.

12. The inflatable splint of claim 1, further comprising:
- a palm portion comprising a plurality of palm chambers, the palm portion adjacent the plurality of volar arm chambers; and wherein when the splint is worn by a user and when each of the plurality of palm chambers are inflated, a palm of a hand of the user is stabilized by the splint.

13. The inflatable splint of claim 1, further comprising:

a forearm bladder having an inflation tube coupled thereto, the forearm bladder coupled to an inner portion of the splint and configured for inflation while the splint is worn by the user so to further stabilize the arm at or near a wrist.

14. The inflatable splint of claim 1, wherein the volar portion and the dorsal portion are coupled to one another via a connection portion located therebetween.

15. A method of stabilizing a forearm, comprising the steps of:

positioning the inflatable splint of claim 1 around a forearm of a user;

securing the splint about the forearm using the first forearm stabilization strap; and inflating each of the first dorsal arm chamber, the second dorsal arm chamber, the third dorsal arm chamber, the first volar arm chamber, the second volar arm chamber, and the third volar arm chamber to stabilize the forearm using the splint.

16. An inflatable splint comprising:

a volar portion comprising a first volar arm chamber, a second volar arm chamber, a third volar arm chamber, a fourth volar arm chamber, and a fifth volar arm chamber, each parallel to one another;

a dorsal portion comprising a first dorsal arm chamber, a second dorsal arm chamber, and a third dorsal chamber, each parallel to one another;

a plurality of hand chambers adjacent the first dorsal arm chamber, the second dorsal arm chamber, and the third dorsal arm chamber; and a first forearm stabilization strap and a second forearm stabilization strap, each extending from the dorsal portion and configured to wrap around the splint when the splint is worn by a user;

wherein when the splint is worn by a user and when each of the first volar arm chamber, the second volar arm chamber, and the third volar arm chamber are inflated, a lengthwise volar portion of a forearm is stabilized by the splint;

wherein a first volar valve is configured to inflate each of the first volar arm chamber, the second volar arm chamber, the third volar arm chamber, the fourth volar arm chamber, and the fifth volar arm chamber;

wherein when the splint is worn by a user and when wherein each of the first dorsal arm chamber, the second dorsal arm chamber, and the third dorsal arm chamber are inflated, a lengthwise dorsal portion of a forearm is stabilized by the splint; and wherein a first dorsal valve is configured to inflate each of the first dorsal arm chamber, the second dorsal arm chamber, and the third dorsal arm chamber.

17. The inflatable splint of claim 16, wherein when the splint is worn by a user and when each of the plurality of hand chambers are inflated, a back of a hand of the user is stabilized by the splint, and wherein the first dorsal valve is further configured to inflate the plurality of hand chambers.

18. The inflatable splint of claim 16, further comprising:

a palm portion comprising a plurality of palm chambers; and wherein when the splint is worn by a user and when each of the plurality of palm chambers are inflated, a palm of a hand of the user is stabilized by the splint.

19. The inflatable splint of claim 16, further comprising:

a plurality of hook and loop fastener portions positioned upon the splint; and wherein the first forearm stabilization strap and the second forearm stabilization strap are configured to wrap around the splint when the splint is worn by a user and to be secured to the splint using at least one hook and loop fastener portion of the hook and loop fastener portions.

20. The inflatable splint of claim 16, wherein the volar portion and the dorsal portion are coupled to one another via a connection portion located therebetween.

* * * * *